(12) United States Patent
Tamura et al.

(10) Patent No.: US 10,527,237 B2
(45) Date of Patent: Jan. 7, 2020

(54) ILLUMINATION APPARATUS

(71) Applicant: OLYMPUS CORPORATION, Tokyo (JP)

(72) Inventors: Kazuaki Tamura, Hachioji (JP);
Masahiro Nishio, Hachioji (JP);
Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 103 days.

(21) Appl. No.: 15/835,530

(22) Filed: Dec. 8, 2017

(65) Prior Publication Data

US 2018/0100627 A1    Apr. 12, 2018

Related U.S. Application Data

(63) Continuation of application No. PCT/JP2015/066735, filed on Jun. 10, 2015.

(51) Int. Cl.
 *F21K 9/64* (2016.01)
 *F21V 9/30* (2018.01)
 (Continued)

(52) U.S. Cl.
 CPC ............. *F21K 9/64* (2016.08); *F21V 5/002* (2013.01); *F21V 9/30* (2018.02); *G02B 23/2469* (2013.01);
 (Continued)

(58) Field of Classification Search
 CPC ........... F21K 9/64; A61B 1/0653; A61B 1/07; G02B 23/2469; G02B 2207/113; F21V 9/30
 See application file for complete search history.

(56) References Cited

U.S. PATENT DOCUMENTS

2006/0099449 A1    5/2006  Amano et al.
2006/0198418 A1*   9/2006  Hama ................. A61B 1/00096
                                                      372/108
(Continued)

FOREIGN PATENT DOCUMENTS

JP    2008-021973 A    1/2008
JP    2013-244297 A    12/2013
(Continued)

OTHER PUBLICATIONS

Machine translation of Yoneda et al., WO 2010/123059, published Oct. 28, 2010 (Year: 2010).*

(Continued)

*Primary Examiner* — William N Harris
(74) *Attorney, Agent, or Firm* — Scully, Scott, Murphy & Presser, P.C.

(57) ABSTRACT

An illumination apparatus includes a first wavelength converter which absorbs part of the first excitation light and emits first wavelength-converted light, a second wavelength converter which absorbs part of the first excitation light and emits second wavelength-converted light, a reflector including a reflecting surface which is arranged to surround the members, and a holder which holds the members. A first region where light distribution angles of light emitted from the members have a predetermined value or less and a second region where the light distribution angle is less than the predetermined value are present in a region surrounded by the reflecting surface. The holder holds at least one part of the wavelength converter and at least one part of the second wavelength converter at the first region.

26 Claims, 14 Drawing Sheets

(51) Int. Cl.
  *F21V 5/00*    (2018.01)
  *G02B 23/24*   (2006.01)
  *F21Y 115/30*  (2016.01)
  *F21Y 113/10*  (2016.01)
  *F21V 23/00*   (2015.01)

(52) U.S. Cl.
  CPC ......... *F21V 23/003* (2013.01); *F21Y 2113/10* (2016.08); *F21Y 2115/30* (2016.08); *G02B 23/2484* (2013.01); *G02B 2207/113* (2013.01)

(56) References Cited

U.S. PATENT DOCUMENTS

| | | | |
|---|---|---|---|
| 2008/0089089 A1* | 4/2008 | Hama | A61B 1/0653 362/574 |
| 2010/0172148 A1* | 7/2010 | Komazaki | A61B 1/0653 362/551 |
| 2013/0206971 A1 | 8/2013 | Kamimura et al. | |
| 2014/0340926 A1* | 11/2014 | Komukai | G02B 23/2469 362/553 |
| 2015/0009703 A1* | 1/2015 | Morizumi | G02B 6/0008 362/553 |

FOREIGN PATENT DOCUMENTS

| | | |
|---|---|---|
| JP | 2014-154313 A | 8/2014 |
| JP | 2014-171511 A | 9/2014 |
| WO | 2010/123059 A1 | 10/2010 |
| WO | WO 2012/144522 A1 | 10/2012 |
| WO | WO 2012/144552 A1 | 10/2012 |

OTHER PUBLICATIONS

Japanese Office Action dated Sep. 4, 2018 in Japanese Patent Application No. 2017-523024.
English translation of International Preliminary Report on Patentability dated Dec. 21, 2017 together with the Written Opinion received in related International Application No. PCT/JP2015/066735.
International Search Report dated Sep. 15, 2015 issued in PCT/JP2015/066735.
Extended Supplementary European Search Report dated Jan. 18, 2019 in European Patent Application No. 15 89 4928.9.
Japanese Office Action dated May 21, 2019 in Japanese Patent Applicaton No. 2017-523024.
Chinese Office Action dated Apr. 1, 2019 in Chinese Patent Application No. 201580080779.5.

* cited by examiner

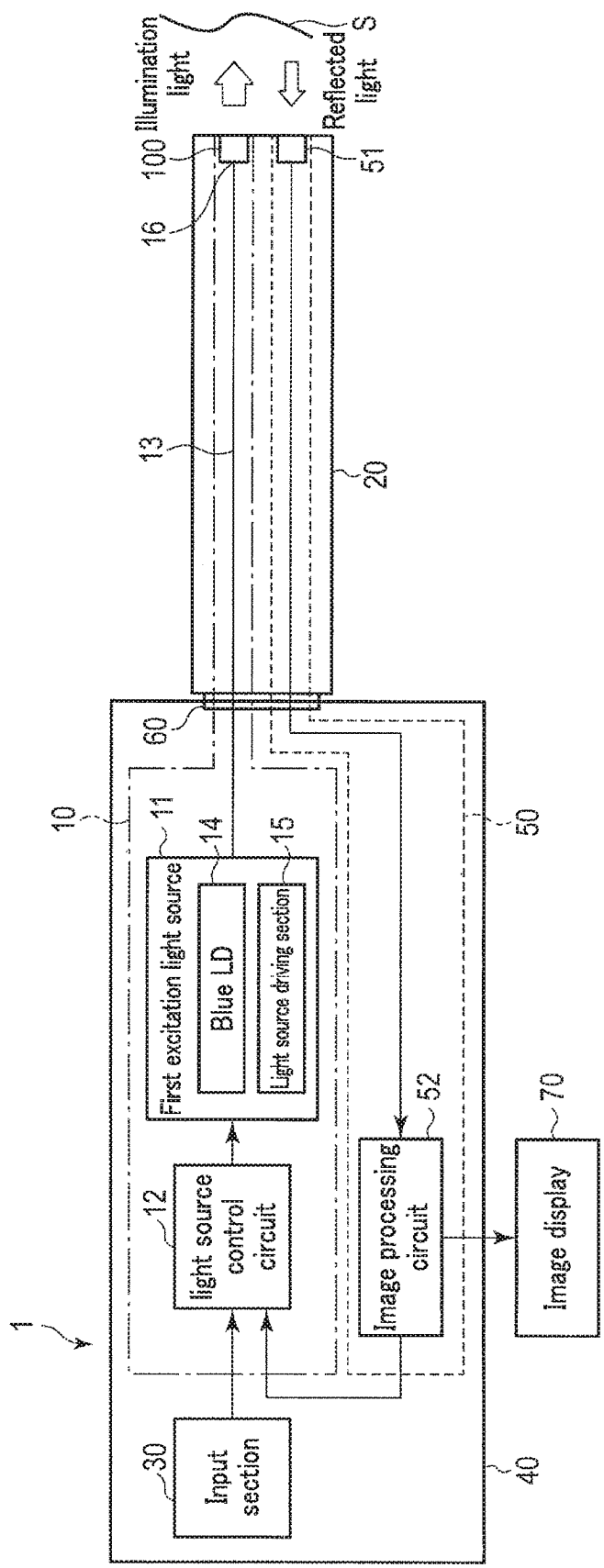
F I G. 1

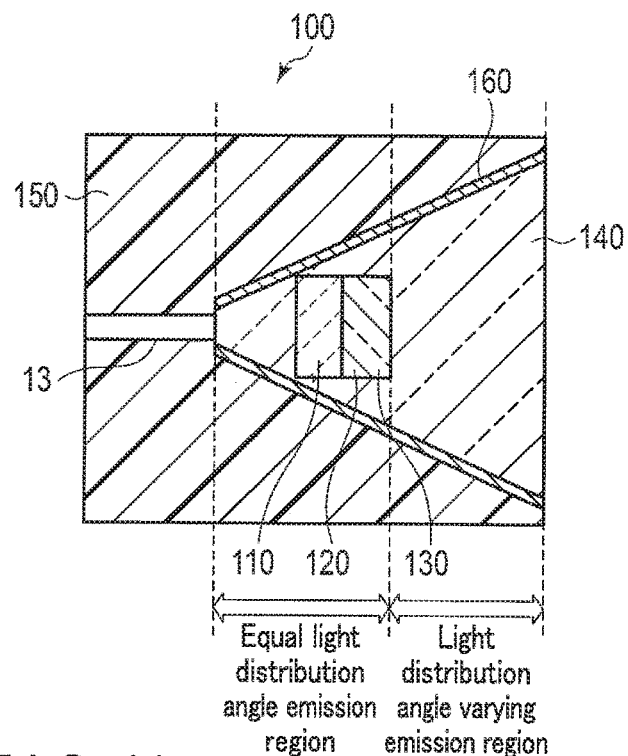
F I G. 11
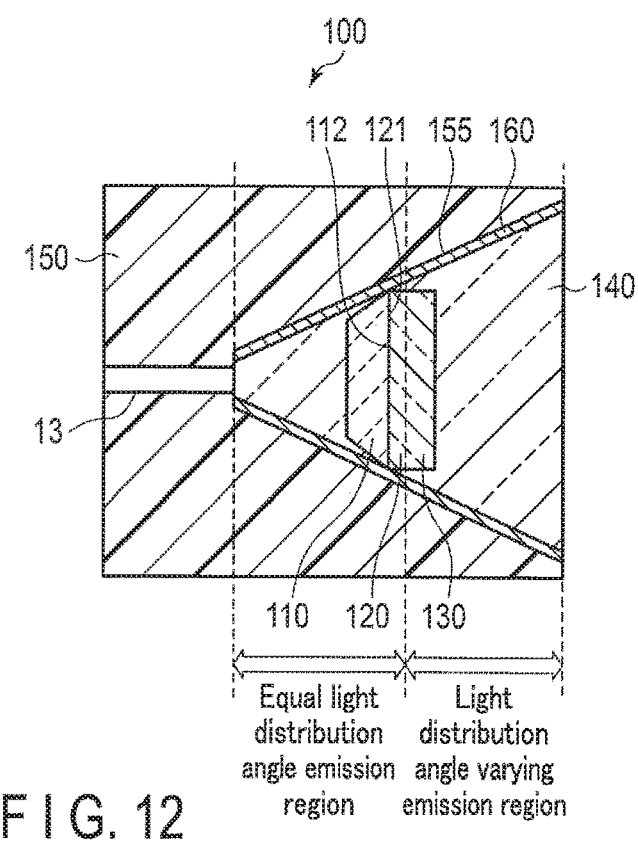
F I G. 12

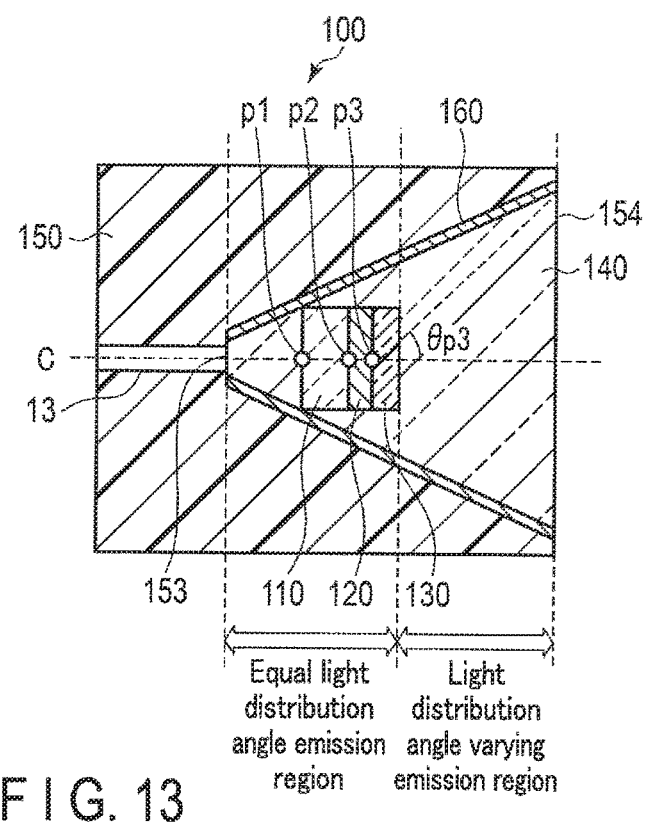
F I G. 13
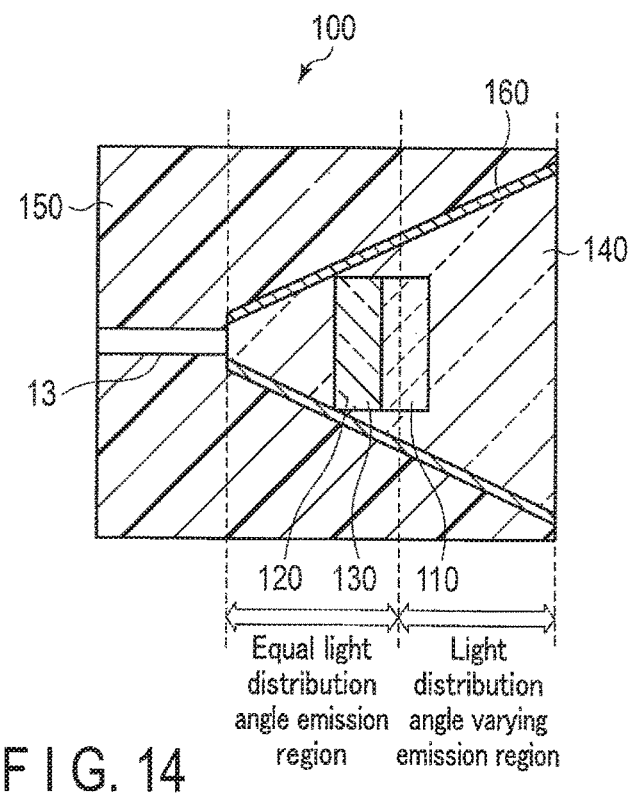
F I G. 14

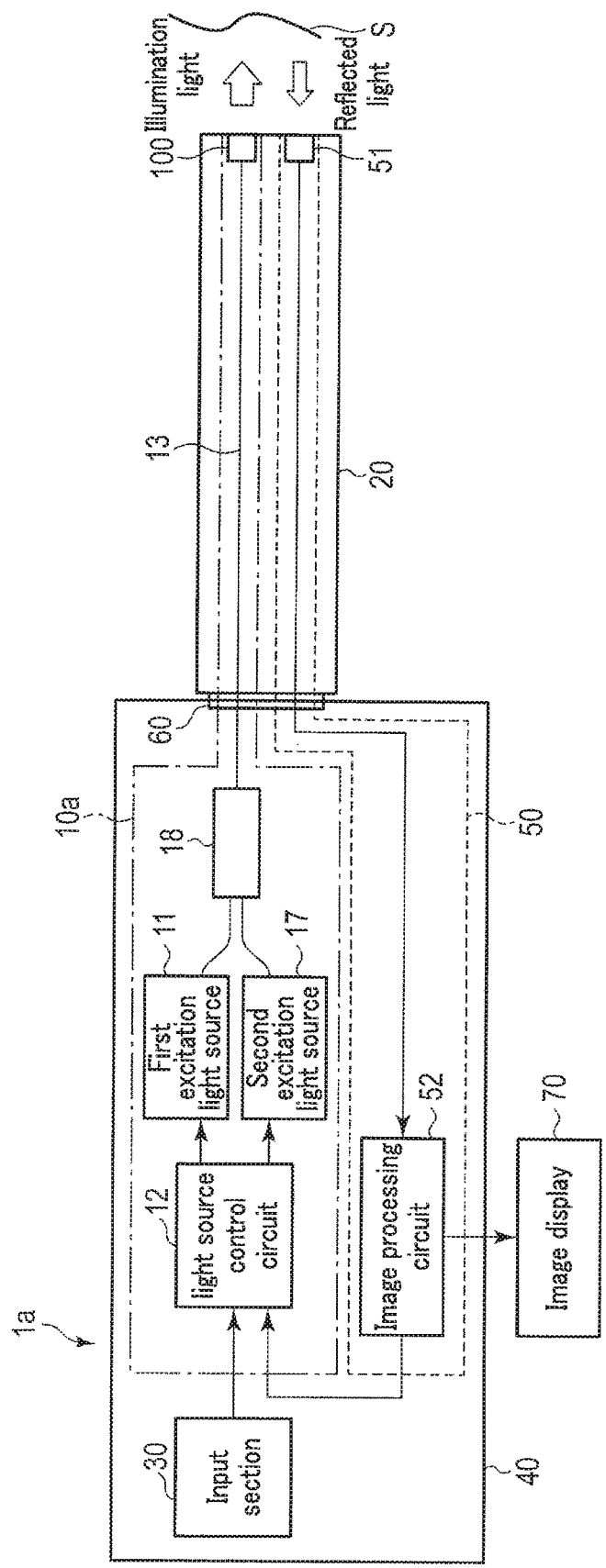
F I G. 16

ILLUMINATION APPARATUS

CROSS-REFERENCE TO RELATED APPLICATIONS

This application is a Continuation Application of PCT Application No. PCT/JP2015/066735, filed Jun. 10, 2015, the entire contents of which are incorporated herein by references.

BACKGROUND OF THE INVENTION

1. Field of the Invention

The present invention relates to an illumination apparatus that emits a plurality of wavelength-converted light beams as illuminating light.

2. Description of the Related Art

An illumination apparatus has been proposed, which guides excitation light, emitted from a small solid-state light source, through an optical fiber and wavelength-converts the excitation light by a wavelength conversion member disposed at the distal end of the optical fiber to emit illuminating light for a desired irradiation pattern and the like.

For example, Jpn. Pat. Appin. KOKAI Publication No. 2008-21973 discloses a light emitting device including a light source that emits excitation light, a light guide member that guides the excitation light from the light source, and a wavelength conversion member that receives the guided excitation light, absorbs at least part of the excitation light and emits light (wavelength-converted light) whose wavelength differs from the wavelength of the excitation light.

BRIEF SUMMARY OF THE INVENTION

One embodiment of the present invention is an illumination apparatus comprising a first wavelength converter which absorbs part of the first excitation light emitted from a first excitation light source and emits first wavelength-converted light that is light in a wavelength region that differs from a wavelength region of the first excitation light, a second wavelength converter which absorbs part of the first excitation light and emits second wavelength-converted light that is light whose wavelength differs from a wavelength of the first excitation light and the first wavelength-converted light, a reflector including a reflecting surface which is arranged to surround the first wavelength converter and the second wavelength converter, the reflector reflecting the first wavelength-converted light and the second wavelength-converted light on the reflecting surface thereof, and a holder which holds the first wavelength converter and the second wavelength converter, wherein the illumination apparatus emits a first illumination light including the first wavelength conversion light and the second wavelength conversion light reflected on the reflector, wherein a first region where light distribution angles of light emitted from each of the first wavelength converter and the second converter have a predetermined value or less and a second region where the light distribution angle is less than the predetermined value are present in a region surrounded by the reflecting surface, wherein the holder holds at least one part of the first wavelength converter and at least one part of the second wavelength converter are at the first region.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 1 is a schematic diagram of an endoscope system including an illumination apparatus according to a first embodiment.

FIG. 11 is a diagram schematically showing a wavelength conversion unit according to modification 2 of the first embodiment.

FIG. 12 is a diagram schematically showing a wavelength conversion unit according to modification 3 of the first embodiment.

FIG. 13 is a diagram schematically showing a wavelength conversion unit according to modification 4 of the first embodiment.

FIG. 14 is a diagram schematically showing a wavelength conversion unit according to modification 5 of the first embodiment.

FIG. 16 is a schematic diagram of an endoscope system including an illumination apparatus according to a third embodiment.

DETAILED DESCRIPTION OF THE INVENTION

Figure 2:
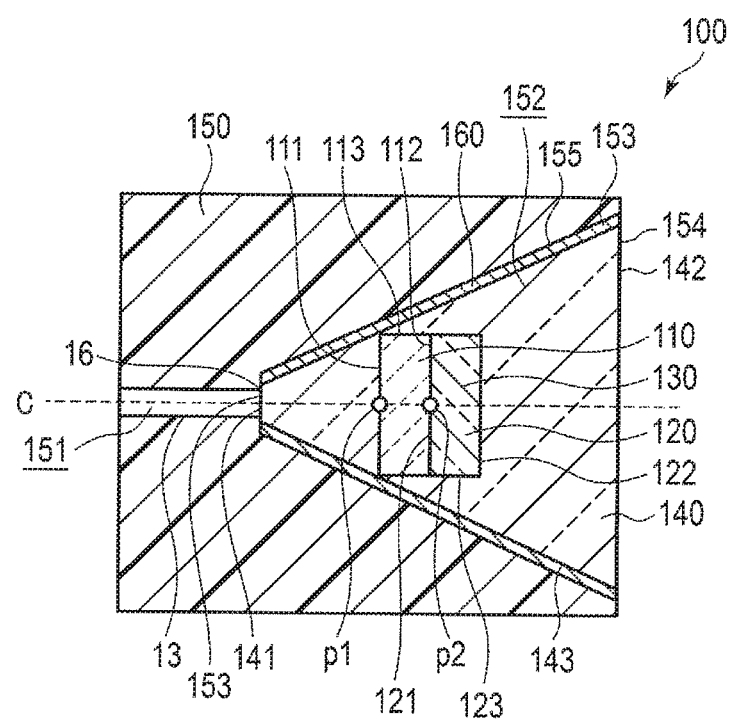
FIG. 2 is a diagram schematically showing a wavelength conversion unit of the illumination apparatus according to the first embodiment.

[First Embodiment]
(Configuration)

FIG. 1 is a schematic diagram of an endoscope system 1 including an illumination apparatus 10 according to a first embodiment. The endoscope system 1 includes an illumination apparatus 10 that irradiates a subject S to be observed with illumination light, an input unit 30 serving as a user interface, which sets the intensity of illumination light of the illumination apparatus 10, and the like, an image acquirement device 50 that acquires an image of the subject S by light reflected from the subject S, and an image display 70 that displays an image of the subject S.

The endoscope system 1 also includes an insertion section 20 whose distal end is, for example, to be inserted into a lumen, a main body section 40, and a connector 60 for detachably connecting the insertion section 20 and the main body section 40. The illumination apparatus 10 and the image acquirement device 50 are disposed ranging from the insertion section 20 to the connector 60 and the main body section 40. The input section 30 is disposed in the main body section 40. The image display 70 is separate from the insertion section 20, the main body section 40, and the connector 60.

The illumination apparatus 10 includes a first excitation light source 11 that emits first excitation light, a light source control circuit 12, an optical fiber 13 that guides the first excitation light from the first excitation light source 11, and a wavelength conversion unit 100 including a first wavelength converter 110 (see FIG. 2) which receives the first excitation light guided by the optical fiber 13 and converts part of the first excitation light into first wavelength-converted light and a second wavelength converter 120 (see FIG. 2) which converts other part of the first excitation light into second wavelength-converted light. The wavelength of the first wavelength-converted light and the wavelength of the second wavelength-converted light are different from the wavelength of the first excitation light. The wavelength conversion unit 100 also includes a diffusion member 130 that converts light distribution characteristics without changing the wavelength of the first excitation light. In the present embodiment, the first wavelength-converted light and the second wavelength-converted light, which are obtained by wavelength-converting part of the first excitation light by the first wavelength converter 110 and the second wavelength converter 120, and the first excitation light diffused light obtained by subjecting part of the first excitation light to light distribution conversion by the diffusion member 130, are radiated to the forward irradiation region from the wavelength conversion unit 100 and used as illumination light to be emitted to the subject S to be observed. The configuration of the illumination apparatus 10 will be described in detail later.

The input section 30 includes a user interface having a power supply operation (ON/OFF) of the illumination apparatus 10, a function of setting the intensity of illumination light emitted from the illumination apparatus 10, and the like. A user's instruction is input to the input section 30 from an input device such as a keyboard and a mouse, neither of which is shown.

The image acquirement device 50 includes an image sensor 51 and an image processing circuit 52. The image sensor 51 includes an image pickup device such as a CCD, and is included in the insertion section 20 and disposed at the distal end thereof. The image sensor 51 converts an optical image, which is obtained from illumination light emitted from the illumination apparatus 10 and then reflected by the subject S, into an electrical signal. The image processing circuit 52 is electrically connected to the image sensor 51 and disposed in the main body section 40. The image processing circuit 52 generates an image signal of the subject S based on the electrical signal from the image sensor 51.

The image display 70 is connected to the image processing circuit 52 of the image acquirement device 50. The image display 70 is a general display device such as a liquid crystal display to display an image of the subject S based on the image signal generated by the image processing circuit 52.

The illumination apparatus 10 will be described in detail.

As described above, the illumination apparatus 10 includes a first excitation light source 11, a light source control circuit 12, an optical fiber 13 and a wavelength conversion unit 100. The first excitation light source 11 and the light source control circuit 12 are disposed in the main body section 40. The optical fiber 13 is disposed ranging from the insertion section 20 to the connector 60 and the main body section 40. The wavelength conversion unit 100 is included in the insertion section 20 and disposed at the distal end thereof.

The first excitation light source 11 includes a laser diode (hereinafter referred to as a blue LD) 14 which emits blue laser light with an emission wavelength peak of 445 nm and a light source driving section 15 for driving the blue LD 14. The first excitation light in the present embodiment is defined as blue laser light with a wavelength peak of 445 nm.

The light source control circuit 12 is connected to the first excitation light source 11. Further, the input section 30 and the image acquirement device 50 (image processing circuit 52) are connected to the light source control circuit 12. The light source control circuit 12 receives light intensity control information for the illumination light output from the input section 30 or light intensity control information output from the image acquirement device 50. Based on these items of control information, the light source control circuit 12 transmits a control signal for driving the blue LD 14 at a predetermined driving current and at predetermined driving intervals to the light source driving section 15.

The optical fiber 13 is a light guide member that guides the first excitation light, which is emitted from the first excitation light source 11, to the wavelength conversion unit 100. The incidence end of the optical fiber 13 is connected to the first excitation light source 11. The emission end of the optical fiber 13 (hereinafter referred to as an optical fiber emission end 16) is connected to the wavelength conversion unit 100. The optical fiber 13 in the present embodiment is, for example, a multimode optical fiber with a core diameter of 50 µm and a numerical aperture FNA of 0.2.

The wavelength conversion unit 100 is disposed beside the optical fiber emission end 16. The wavelength conversion unit 100 receives the first excitation light emitted from the optical fiber emission end 16. Then, the wavelength conversion unit 100 converts part of the received first excitation light into first wavelength-converted light and second wavelength-converted light each having wavelength characteristics and light distribution characteristics, which differ from those of the first excitation light. The wavelength conversion unit 100 also converts part of the received first excitation light into first excitation light diffused light whose enlarged light distribution angle is increased. Therefore, the wavelength conversion unit 100 emits, as illumination light, emission light composed of three optical components of a first optical component (first wavelength-converted light), a second optical component (second wavelength-converted light) and a third optical component (first excitation light diffused light). The light distribution characteristics of the first wavelength-converted light, the second wavelength-converted light and the first excitation light diffused light, emitted from the wavelength conversion unit 100, do not vary with the intensity of incident first excitation light, but are fixed.

FIG. 2 is a diagram schematically showing the wavelength conversion unit 100. The wavelength conversion unit 100 includes a first wavelength converter 110, a second wavelength converter 120, a diffusion member 130, a transparent member 140, a holder 150 and a reflector 160.

The first wavelength converter 110 in the present embodiment absorbs part of the first excitation light (blue laser light) emitted from the first excitation light source 11 (blue LD 14) to wavelength-convert it into the first wavelength-converted light (yellow fluorescence) which is fluorescence having an emission wavelength peak at 550 nm of the wavelength (yellow region) which is longer than that of the first excitation light. Specifically, for the first wavelength converter 110, a phosphor represented by a composition of $Y_3Al_5O_{12}$:Ce (hereinafter referred to as YAG) is used. The first wavelength converter 110 is polycrystallized YAG ceramics. The YAG ceramics have properties of hardly diffusing excitation light that is transmitted therethrough and have a high thermal conductivity of about 10 W/mK. For the first wavelength converter 110, in addition to the YAG ceramics, ceramics such as YAG single crystal, LAG:Ce, and TAG:Ce can be used as a phosphor.

The first wavelength converter 110 is shaped like a cylinder. The first wavelength converter 110 has, for example, a diameter φ of 0.3 mm and a thickness of 0.1 mm. The first wavelength converter 110 has a circular incident surface 111 on which the first excitation light is incident from the optical fiber emission end 16, a circular emission surface 112 opposed to the incident surface 111, and a side surface 113 that is an outer surface between the incident surface 111 and the emission surface 112. The irradiation region of the first excitation light on the incident surface 111 is smaller than the incident surface 111.

The second wavelength converter 120 in the present embodiment absorbs another part of the first excitation light (blue laser light) emitted from the first excitation light source 11 (blue LD 14) to wavelength-convert it into the second wavelength-converted light (green fluorescence) which is fluorescence having an emission wavelength peak of 540 nm of the wavelength (green region) which is longer than that of the first excitation light. The second wavelength converter 120 contains a powder phosphor and a sealing material for sealing the powder phosphor. Specifically, an Eu-activated oxynitride-based phosphor and an Eu-activated silicate-based phosphor are used as the powder phosphor. The sealing material is, for example, a transparent resin that is a silicone resin.

The second wavelength converter 120 is also shaped like a cylinder and has, for example, a diameter φ of 0.3 mm and a thickness of 0.1 mm. That is, in the present embodiment, the second wavelength converter 120 has the same diameter as that of the first wavelength converter 110. The second wavelength converter 120 has a circular incident surface 121 that is in contact with the emission surface 112 of the first wavelength converter 110, a circular emission surface 122 opposed to the incident surface 121, and a side surface 123 that is an outer surface between the incident surface 121 and the emission surface 122.

In the present embodiment, the diffusion member 130 is mixed with the second wavelength converter 120. The diffusion member 130 in the present embodiment expands a spread angle of the first excitation light (blue laser light) which has entered the diffusion member 130, without changing its wavelength and converts the light into the first excitation light diffused light (blue laser diffused light) having weakened coherence. Specifically, the diffusion member 130 is alumina diffusion particles whose refractive index (refractive index 1.7) is higher than the refractive index (refractive index 1.4) of the sealing material of the second wavelength converter 120, and the alumina diffusion particles are dispersed in the sealing material. Thus, the diffusion particles are reflective diffusion particles or transmissive diffusion particles having a refractive index that is higher than that of the transparent member 140.

The difference between the spread angle of the light incident on the diffusion member 130 in the second wavelength converter 120 and the spread angle of the light emitted from the diffusion member 130, namely, the increase angle of the spread angle is determined chiefly by the diameter of the diffusion particles, the concentration of the diffusion particles relative to the sealing material, the refractive index of the diffusion particles and the sealing material, the thickness of the entire second wavelength converter 120, and the like. In the present embodiment, a predetermined diffusion concentration condition and the like are set in such a manner that the light distribution angle of the first excitation light diffused light becomes equal to the angle between the light distribution angle (narrow light distribution angle) at which the first wavelength-converted light and the second wavelength-converted light are emitted from the emission surface 142 (described later) of the transparent member 140 and the first wavelength conversion light distribution angle and the second wavelength conversion light distribution angle (nondirectivity) at which light is emitted from the first wavelength converter 110 and the second wavelength converter 120.

The transparent member 140 is made of high-transmittance glass, silicone resin or the like. The transparent member 140 transmits the first excitation light, the first wavelength-converted light, the second wavelength-converted light and the first excitation light diffused light. Instead of the transparent member 140, a transparent region such as a gap through which the first excitation light, the first wavelength-converted light, the second wavelength-converted light and the first excitation light diffused light pass, may be disposed.

The transparent member 140 is shaped like a truncated cone, inside which the first wavelength converter 110 and the second wavelength converter 120 (the diffusion member 130) are disposed. The transparent member 140 has a small-diameter circular incident surface 141 on which the first excitation light is incident from the optical fiber emission end 16, a large-diameter circular emission surface 142 opposed to the incident surface 141, and a side surface 143 that is an outer surface between the incident surface 141 and the emission surface 142. The size of the incident surface 141 is equal to or larger than that of the optical fiber emission end 16. The incident surface 141 is optically connected to the optical fiber emission end 16.

The holder 150 holds the optical fiber emission end 16, the first wavelength converter 110, the second wavelength converter 120, the diffusion member 130 and the transparent member 140. The holder 150 is shaped like, for example, a cylinder. In addition, the holder 150 has a cylinder-shaped hollow portion 151 in which the optical fiber emission end 16 is disposed and a truncated-cone-shaped hollow portion 152 whose diameter increases in the emission direction (axial direction) of the first excitation light from the optical fiber emission end 16. The hollow portions 151 and 152 extend continuously in the axial direction around the central axis C of the holder 150 and pass through the inside of the holder 150.

The hollow portion 152 includes a holder incidence portion 153 that is an opening where the incident surface 141 of the transparent member 140 is disposed, and a holder emission portion 154 that is an opening where the emission surface 142 thereof is disposed. The hollow portion 152 is a through hole extending from the holder incidence portion 153 to the holder emission portion 154, and is tapered such that its diameter increases from the holder incidence portion 153 to the holder emission portion 154. In other words, a taper surface 155 is formed by the inner surface of the hollow portion 152. The first excitation light enters the holder incidence portion 153 from the optical fiber emission end 16. The holder emission portion 154 emits the first wavelength-converted light, the second wavelength-converted light and the first excitation light diffused light.

In the hollow portion 152, the transparent member 140, the first wavelength converter 110, the second wavelength converter 120 (diffusion member 130) and the transparent member 140 are arranged and held in order from the optical fiber emission end 16. The emission surface 142 of the transparent member 140 and the end face of the holder emission portion 154 are substantially flush with each other. Therefore, the emission surface 122 of the second wavelength converter 120 exists inside the end face of the holder emission portion 154.

The central axis C of the holder 150 is coaxial with the optical path axis of the first excitation light emitted from the optical fiber emission end 16. The first wavelength converter 110 and the second wavelength converter 120 are laminated in the hollow portion 152 such that they are symmetrical (rotationally symmetrical) with regard to the central axis C of the holder 150. In the present embodiment, only the edge portion of the incident surface 111 on which the first excitation light is incident in the first wavelength converter 110 is in contact with the entire circumference of the taper surface 155, and the side surface 113 of the first wavelength converter 110 is separated from the taper surface 155. The side surface 123 of the second wavelength converter 120 is completely separated from the taper surface 155.

The taper angle of the holder 150 is defined as an inclination angle formed by the taper surface 155 that is the inner surface of the truncated cone and the central axis C of the holder 150. In order to extract the nondirectivity first wavelength-converted light and second wavelength-converted light and the first excitation light, which is diffused light diffused by the diffusion member 130, efficiently from the wavelength conversion unit 100, it is favorable that the taper angle be about 10° to 60°. Specifically, the wavelength conversion unit 100 (holder 150) in the present embodiment has a taper angle of 25°, an incident diameter of 0.07 mm, an emission diameter of 0.7 mm and a thickness of 0.675 mm.

On the taper surface 155 of the holder 150, a reflector 160 is formed. The reflector 160 in the present embodiment is a metal reflecting film (reflecting mirror) which is formed by plating a thin metal such as silver and aluminum on the taper surface 155. When the first excitation light, the first wavelength-converted light, the second wavelength-converted light and the first excitation light diffused light enters the reflector 160, the reflector 160 performs specular reflection or diffuse reflection of the light that has entered. In other words, the reflector 160 is disposed such that the light distribution conversion amount of light emitted at a predetermined light distribution angle from a position on the central axis C connecting the holder incidence portion 153 and the holder emission portion 154 is changed by the reflection.

The first excitation light emitted from the optical fiber emission end 16 is radiated most strongly on the central axis C. The position at which the first excitation light is radiated most strongly to the first wavelength converter 110 is a point of the intersection of the incident surface 111 of the first wavelength converter 110 and the central axis C, and it is also a position at which the intensity of the first wavelength-converted light obtained by absorbing part of the excitation light becomes high. This position is defined as a substantial light emission point p1 of the first wavelength converter 110. Similarly, the position at which the first excitation light is radiated most strongly to the second wavelength converter 120 is a point of the intersection of the incident surface 121 of the second wavelength converter 120 and the central axis C, and it is also a position at which the intensity of the second wavelength-converted light becomes high. This position is therefore defined as the substantial light emission point p2 of the second wavelength converter 120. In the present embodiment, since the diffusion member 130 is included in the second wavelength converter 120, the position p2 is also a substantial diffusion point p3 of the diffusion member 130.

The position of the light emission point at which the illumination apparatus 10 emits illumination light (narrow-distributed light) having a high center intensity with uniform light distribution of the first wavelength-converted light, the second wavelength-converted light and the first excitation light diffused light, will be described below.

First, the relationship between the position of the light emission point in the holder 150, which corresponds to the taper angle of 25° and the light distribution characteristic of the light emitted from the wavelength conversion unit 100 will be described.

Figure 3:
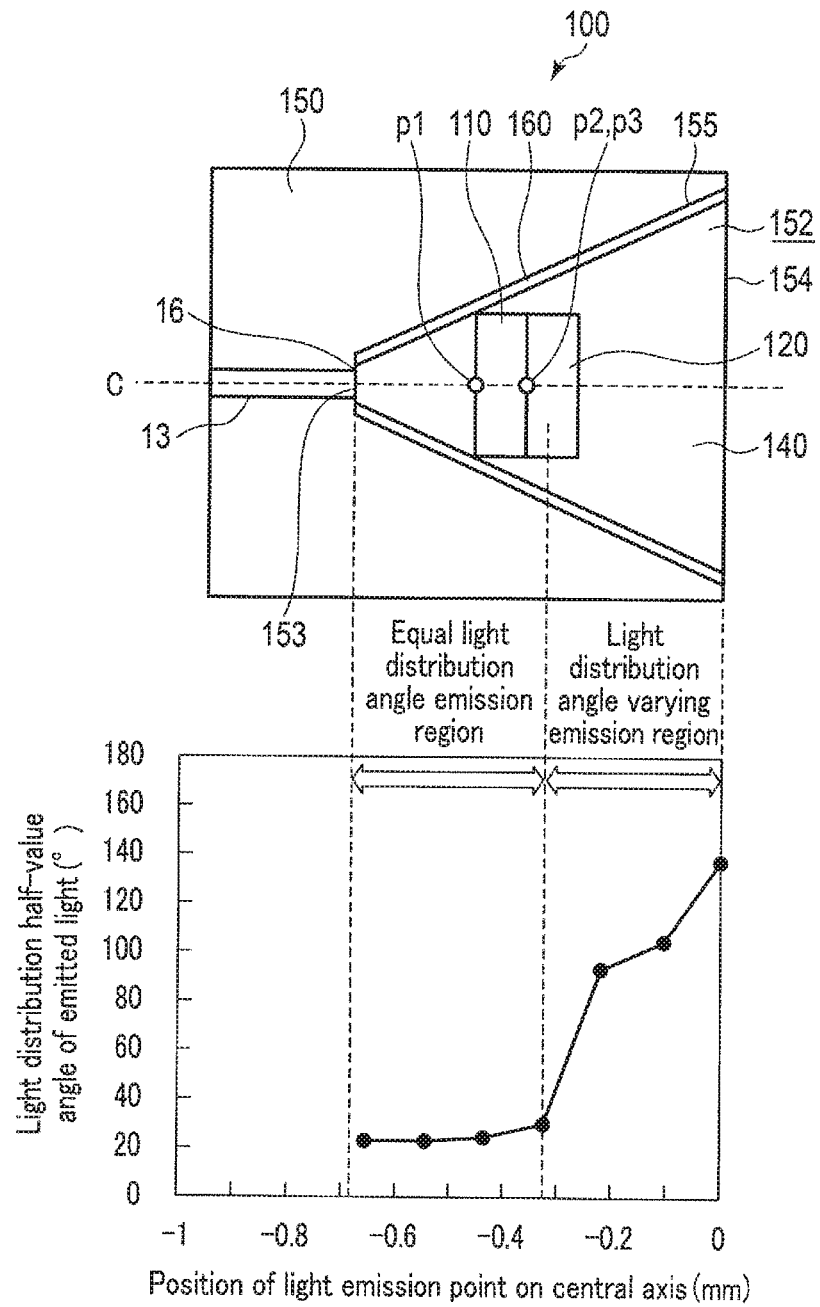
FIG. 3 is a diagram showing the relationship between the position of a light emission point of the wavelength conversion unit of the illumination apparatus according to the first embodiment and the light distribution half-value angle of emitted light.

FIG. 3 is a diagram showing the relationship between the light distribution characteristics of light emitted from the wavelength conversion unit 100 when a nondirectivity point light source is located at a position on the central axis C in the holder 150 (hollow portion 152), namely, the position of a light emission point and the light distribution half-value angle of the emitted light. In the graph shown in FIG. 3, the position of the light emission point of the point light source, which is on the horizontal axis, is based on the end face of the holder emission portion 154.

The leftmost plot (position: −0.65 mm) in the graph of FIG. 3 shows light distribution characteristics when the point light source is disposed very close to the optical fiber emission end 16 (the end face of the holder incident portion 153). Here, the nondirectivity light emitted from the point light source is reflected repeatedly by the reflector 160 formed on the taper surface 155. As a result, the light distribution half-value angle of the emitted light is about 22°, indicating the light distribution characteristics of narrow light distribution.

Even though the point light source moves on the central axis C from the immediate vicinity of the optical fiber emission end 16 to the vicinity of the center (position: −0.325 mm) of the hollow portion 152 of the holder 150, the light distribution half-value angle of the emitted light hardly varies (gradually increases) and, for example, the characteristics of narrow light distribution of about 30° are shown at the position of −0.325 mm. In other words, FIG. 3 shows that the light distribution characteristics of the emitted light varies little at the position on the central axis C of the point light source from the optical fiber emission end 16 to the vicinity of the center of the hollow portion 152. At the position of the point light source from the optical fiber emission end 16 to the vicinity of the center portion of the holder 150, most of the light emitted from the wavelength conversion unit 100 has components of light which is emitted backward, laterally and forward from the point light source, reflected by the taper surface 155 and then emitted in a different direction and has few components directly emitted forward. It is thus inferred that a region from the optical fiber emission end 16 to the vicinity of the central part of the holder 150 is influenced little by a position.

When the point light source moves on the central axis C from the vicinity of the center (position: −0.325 mm) of the hollow portion 152 to the holder emission portion 154, the light distribution half-value angle of the emitted light increases sharply. In other words, FIG. 3 shows the characteristics that as the point light source moves toward the holder emission portion 154 from the vicinity of the center of the hollow portion 152, the light distribution half-value angle of the emitted light is increased. When the point light source is disposed on the end face of the holder emission portion 154, the light distribution half-value angle is about 140°, indicating the light distribution characteristics of wide light distribution.

As described above, toward the holder emission portion 154 from the vicinity of the center of the hollow portion 152 of the holder 150, the position of the light emission point on the central axis C has a great influence upon variations in the light distribution half-value angle of the emitted light. It is considered that toward the holder emission portion 154, the component emitted directly forward from the nondirectivity point light source increases at once, which exerts the influence that the light distribution half-value angle varies so as to increase the light distribution characteristics of the emitted light.

As is seen from the above, when the position of the point light source is changed on the central axis C from the end face of the holder incidence portion 153 to the end face of the holder emission portion 154, a region where the light distribution half-value angle varies little, namely, a region where the difference in the light distribution half-value angle (the amount of variation from the reference position) in the present embodiment falls below Δ20° is defined as "equal light distribution angle emission region" and a region where the light distribution half-value angle varies by Δ20° or more is defined as "light distribution angle varying emission region". In other words, a region surrounded by the reflector 160 in the hollow portion 152 includes an "equal light distribution angle emission region" where the light distribution angles of light emitted from within a predetermined region are substantially equal and a "light distribution angle varying emission region" where the light distribution angles of light emitted from within a predetermined region are different. In the present embodiment, the plane in which the length from the intersection with the end face of the holder incidence portion 153 to the intersection with the end face of the holder emission portion 154 on the central axis C is divided in the ratio of 1.2 (incidence side) to 1 (emission side) is a boundary surface by which the "equal light distribution angle emission region" and the "light distribution angle varying emission region" are separated from each other.

Next, the relationship between the position of the light emission point of the point light source and the angle formed by the light emission point and the emission end will be described below.

Figure 4:
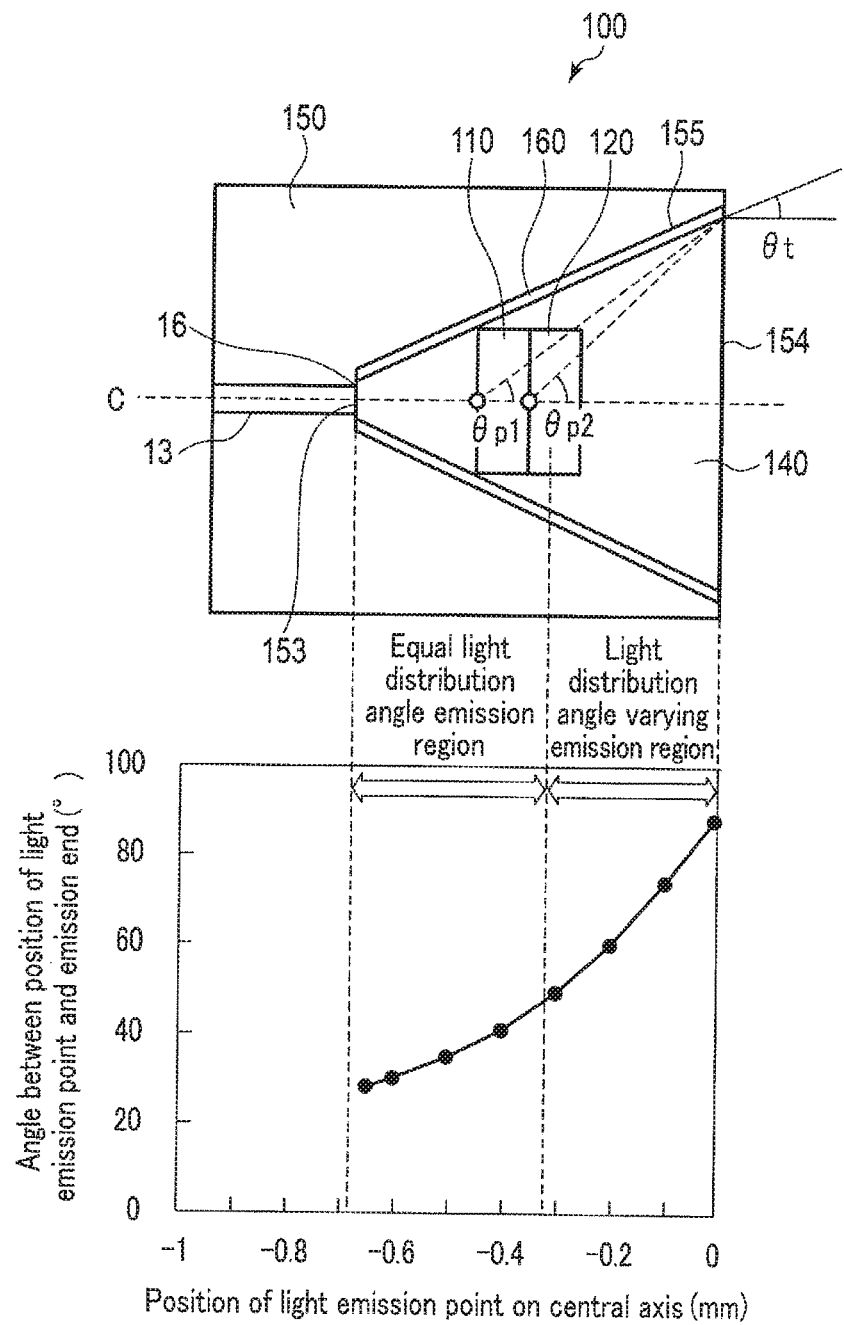
FIG. 4 is a diagram showing the relationship between the position of the light emission point of the wavelength conversion unit of the illumination apparatus according to the first embodiment and the angle formed by the light emission point and the emission end.

FIG. 4 is a diagram showing the relationship between the position of the light emission point and the angle formed by the position of the light emission point and the point on the open end of the holder emission portion 154. In the graph shown in FIG. 4, the horizontal axis is the same as that in FIG. 3, and indicates the position of the light emission point of the point light source on the central axis C. The vertical axis indicates the angle formed by the central axis C and the line connecting the position of the point light source on the central axis C and the point on the open end of the holder emission portion 154. FIG. 4 shows an angle (the direct emission limit angle of the first wavelength-converted light) $\theta p1$ formed by the central axis C and the line connecting the substantial center of the light emission point p1 of the first wavelength converter 110 and the point on the open end of the holder emission portion 154 and an angle (the direct emission limit angle of the second wavelength-converted light) $\theta p2$ formed by the central axis C and the line connecting the substantial center of the light emission point p2 of the second wavelength converter 110 and the point on the open end of the holder emission portion 154. The taper angle $\theta t$ is 25°.

In FIG. 4, the angles $\theta p1$ and $\theta p2$ are small when the point light source is located beside the holder incidence portion 153 (in the immediate vicinity of the optical fiber emission end 16), becomes larger as it moves toward the holder emission portion 154, and intersects with the central axis C at about 90° when it is located near the end face of the holder emission portion 154. Furthermore, the relationship (light distribution characteristics) between the position of the point light source and the light distribution half-value angle of the emitted light is as shown in FIG. 3, and the boundary surface between the "equal light distribution angle emission region" and the "light distribution angle varying emission region" is present near the position of −0.325 mm. In other words, when referring to this angle as an angle between the point light source and the emission end, the boundary between the "equal light distribution angle emission region" and the "light distribution angle varying emission region" corresponds to about 48° from FIG. 4. Therefore, when the taper angle of the holder 150 is 25°, the distribution characteristics of light to be emitted becomes narrow light distribution at the position on the central axis C where the angle $\theta p1$ or $\theta p2$ is about 48° or less.

From the above, in the holder 150 whose taper angle is 25°, a region where the line connecting a point where the incident surface 111 of the first wavelength converter 110 and the incident surface 121 of the second wavelength converter 120 intersect the central axis C and a point on the open end of the holder emission portion 154 is equal to or less than about twice the taper angle θt of the holder 150, is the "equal light distribution emission region."

Since, furthermore, the "equal light distribution angle emission region" of the present embodiment is present beside the holder incidence portion 153, it is defined as an "incidence portion side equal light distribution angle emission region."

(Operation of Illumination Light Performed when First Excitation Light Enters)

Figure 5:
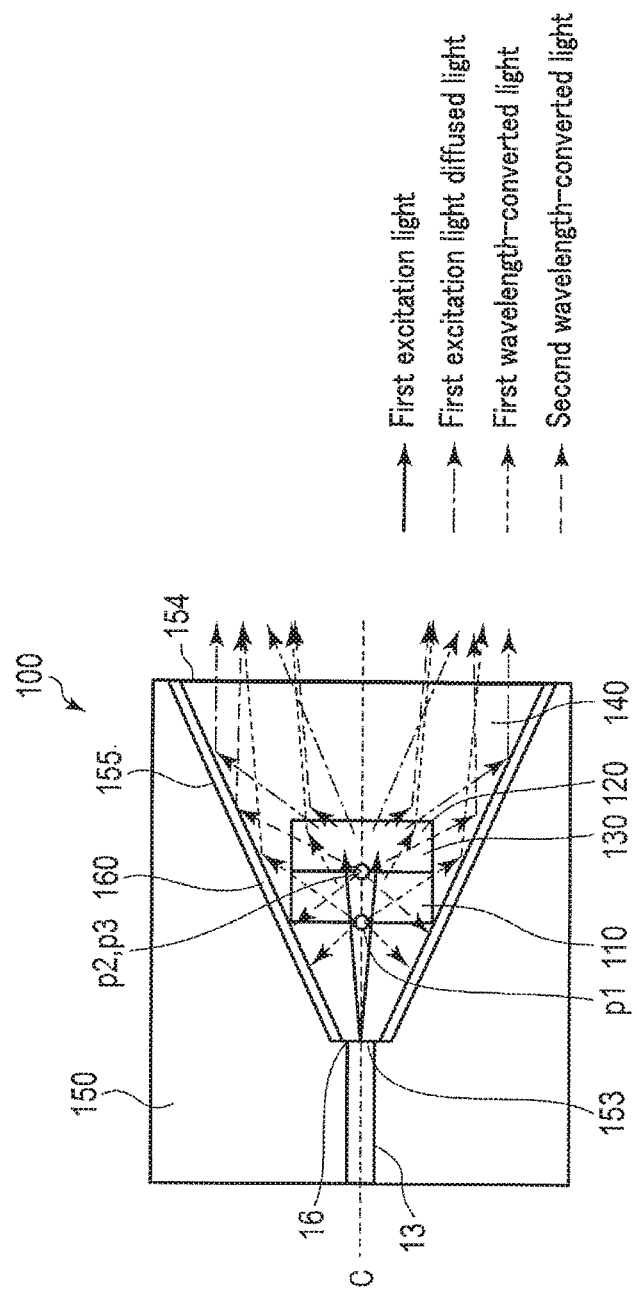
FIG. 5 is a diagram schematically showing the first excitation light, the first wavelength-converted light, the second wavelength-converted light and the first excitation light diffused light inside a holder.

An operation of generating illumination light by the wavelength conversion unit 100 will be described with reference to FIGS. 5 through 7. The first excitation light is guided by the optical fiber 13 and emitted from the optical fiber emission end 16 to the wavelength conversion unit 100. The first excitation light emitted from the optical fiber emission end 16 is narrow-distributed light and the light distribution half-value angle is about 15°.

The first excitation light emitted to the wavelength conversion unit 100 is transmitted through the transparent member 140 and is incident on the incident surface 111 of the first wavelength converter 110. Part of the incident first excitation light is absorbed by the first wavelength converter 110 and other part thereof is transmitted through the first wavelength converter 110. The absorbed first excitation light is wavelength-converted into the first wavelength-converted light, generated from a region including the substantial light emission point p1 of the first wavelength converter 110, and emitted isotropically.

The first wavelength-converted light emitted laterally from the first wavelength converter 110 is reflected by the taper surface 155 of the holder 150, and part of the reflected light is emitted forward from the emission surface 142 (holder emission portion 154) without reentering the first wavelength converter 110 or the second wavelength converter 120 Part of the light emitted backward (toward the optical fiber emission end 16) from the substantial light emission point p1 of the first wavelength converter 110 and part of the light emitted forward is also reflected in a different direction by the taper surface 155, and is emitted forward from the emission surface 142 (holder emission portion 154).

On the other hand, the first excitation light which has not been absorbed by the first wavelength converter 110 is transmitted through the emission surface 112 of the first wavelength converter 110 and is radiated to the incident surface 121 of the second wavelength converter 120. Part of the radiated first excitation light is absorbed by a green powder phosphor included in the second wavelength converter 120. The absorbed second excitation light is wavelength-converted into the second wavelength-converted light, generated from a region including the substantial light emission point p2 of the second wavelength converter 120, and emitted isotropically.

The second wavelength-converted light emitted laterally from the second wavelength converter 120 is also reflected by the taper surface 155 of the holder 150, and part of the reflected light is emitted forward from the emission surface 142 (holder emission portion 154) without reentering the first wavelength converter 110 or the second wavelength converter 120. Part of the light emitted backward (toward the optical fiber emission end 16) from the substantial light emission point p2 of the second wavelength converter 120 and part of the light emitted forward is also reflected in a different direction by the taper surface 155, and is emitted forward from the emission surface 142 (holder emission portion 154).

As described above, the first wavelength converter 110 and the second wavelength converter 120 having substantial light emission points p1 and p2 in the "incident portion side equal light distribution angle emission region" respectively convert the first excitation light having nondirectivity characteristics into the first wavelength-converted light and the second wavelength-converted light having narrow light distribution characteristics. In other words, the distribution of the first wavelength-converted light and that of the second wavelength-converted light are equal. Then, the first wavelength-converted light and the second wavelength-converted light, which are narrow-distributed light, are emitted from the holder emission portion 154 as part of the illumination light.

Part of the first excitation light incident on the second wavelength converter 120 is scattered, reflected, transmitted and diffused by the diffusion member 130 included in the second wavelength converter 120 to generate first excitation light diffused light. The concentration, particle diameter and refractive index of the diffusion particles of the diffusion member 130 with respect to the sealing material of the second wavelength converter 120 are adjusted such that the first excitation light diffused light is emitted at an emission angle that is substantially equal to the light distribution half-value angle of the first wavelength-converted light and the second wavelength-converted light emitted from the holder emission portion 154.

Figure 6:
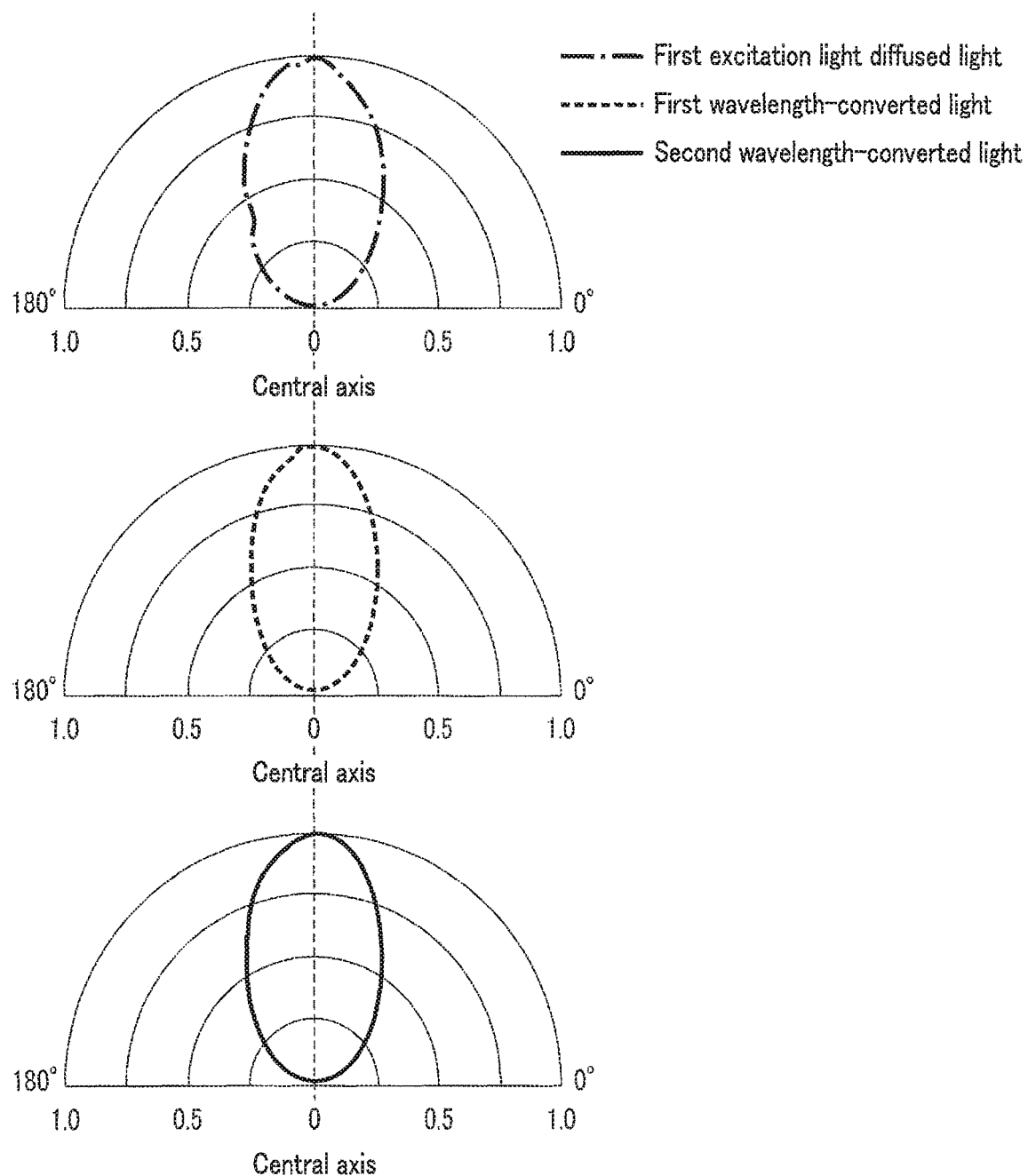
FIG. 6 is a diagram showing an example of light distribution characteristics of illumination light emitted from the wavelength conversion unit.

FIG. 6 is a diagram showing the light distribution characteristics of the first excitation light diffused light, the first wavelength-converted light and the second wavelength-converted light emitted from the holder emission portion 154 of the wavelength conversion unit 100. As described above, the first wavelength converter 110 and the second wavelength converter 120 in the present embodiment are shaped like a cylinder (its diameter φ is 0.3 mm and its thickness is 0.1 mm), and are larger than the point light sources shown in FIG. 3. Therefore, actually, the fluorescence components (first and second fluorescence components) generated from a region other than the substantial light emission points p1 and p2 of the first wavelength converter 110 and the second wavelength converter 120 (other than a point on the central axis C) are reflected by the reflector 160 and emitted with a wider light distribution than the light distribution result at the point light source. As a result, the light distribution half-value angles of the first wavelength-converted light and the second wavelength-converted light by the cylindrical first wavelength converter 110 and second wavelength converter 120 are about 65°. The light distribution half-value angle of the first excitation light diffused light represents the same degree of light distribution characteristics of about 65° by applying predetermined conditions of the diffusion member 130 thereto.

Figure 7:
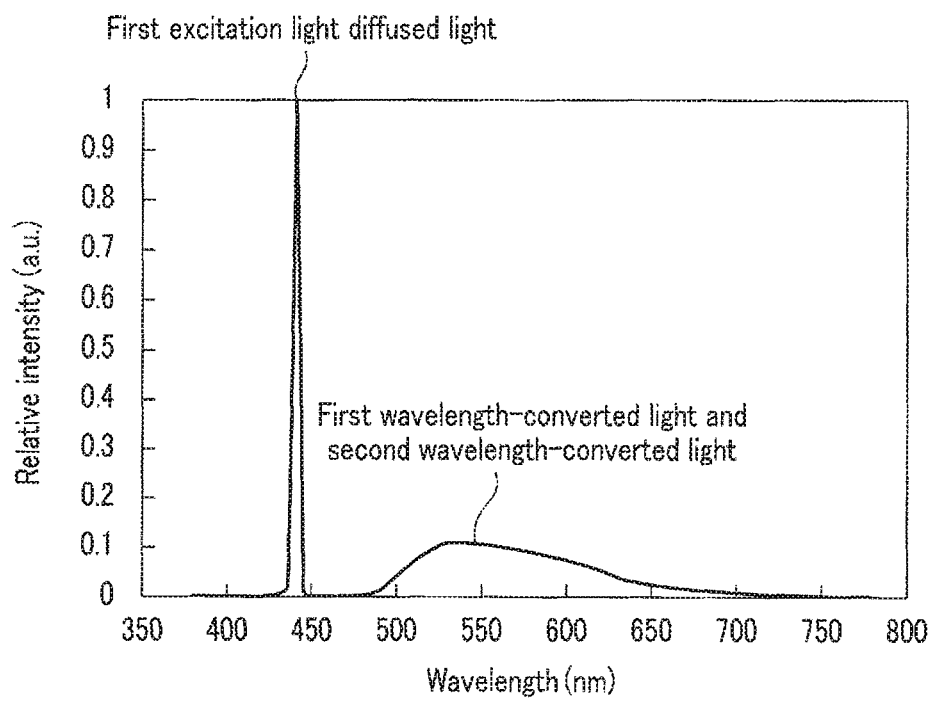
FIG. 7 is a graph showing an example of an emission spectrum of the illumination light in the first embodiment.

FIG. 7 is a diagram showing an example of an emission spectrum of the illumination light. The illumination light is color mixing light of the first excitation light diffused light (blue laser light), the first wavelength-converted light (yellow fluorescent light) and the second wavelength-converted light (green fluorescent light). The illumination light is white light of about 6000 K as a specific correlated color temperature. The emission spectrum is determined by the conditions of the thickness of YAG ceramics of the first wavelength converter 110 and the predetermined concentration and thickness of the green powder phosphor and the diffusion particles of the second wavelength converter 120.

In the present embodiment, the light distributions of the excitation light diffused light and the two wavelength-converted light beams, which constitute the white illumination light, are substantially equal to each other. Thus, the illumination light is emitted forward from the wavelength conversion unit 100 as white light of the same color tone for any illumination angle.

On the other hand, when the light distributions of the excitation light diffused light and the two wavelength-converted light beams are remarkably different, illumination light having an uneven color is emitted. Thus, light distribution characteristics of the illumination light are set in such a manner that the difference in color between the two wavelength-converted light beams and the excitation light diffused light radiated onto the surface of the subject S to be observed falls within a level at which it is almost invisible in the general-purpose image processing of the image acquirement device 50. Specifically, if the illumination light is emitted under one of the following light distribution conditions for the excitation light diffused light and the two wavelength-converted light beams, it is preferably possible to obtain an image of the subject S having almost no color unevenness.

- the difference between the light distribution half-value angle of the excitation light diffused light and that of the two wavelength-converted light beams is 10° or less.
- When the intensity peaks are aligned (on the central axis C, for example), the difference between the light distribution half-value angle of the excitation light diffused light and that of the two wavelength-converted light beams is 15° or less.
- In a light distribution angle region of not less than a predetermined brightness (for example, a light distribution angle of 3/4 or more), the difference in intensity ratio between the excitation light diffused light and the two wavelength-converted light beams is 15% or less.

(Advantages)

According to the present embodiment, the substantial light emission points p1 and p2 of the two wavelength converters 110 and 120 are set in the "equal light distribution angle region" in the hollow portion 152 inside the holder 150 including the taper surface 155 having the diameter-increasing taper angle θt. Thus, even though the positions of the light emission points of the two wavelength converters 110 and 120 are different from each other on the central axis C, it is possible to provide an illumination apparatus capable of emitting two wavelength-converted light beams with their light distribution uniform.

Furthermore, according to the present embodiment, the light distribution of the first excitation light diffused light can be matched to the light distribution of the two wavelength-converted light beams by setting the diffusion member 130 to a predetermined condition (for example, a concentration condition). It is thus possible to emit illumination light in which the light distributions of three light components emitted from the wavelength conversion unit 100 are matched, that is, their color unevenness is reduced. Furthermore, the light distribution of the first excitation light diffused light can be matched to the light distribution of the two wavelength-converted light beams even by setting the substantial diffusion point p3 of the diffusion member 130 in the "incidence portion side equal light distribution angle emission region."

In addition, the intensity near the central axis C of the illumination light emitted from the wavelength conversion unit 100 can be increased by arranging the first wavelength converter 110, the second wavelength converter 120 and the diffusion member 130 symmetrically with regard to the central axis C on the central axis C within the hollow portion 152 inside the holder 150. In other words, it is possible to provide an illumination apparatus capable of emitting illumination light having narrowed-angle light distribution characteristics.

Furthermore, part of the two wavelength-converted light beams emitted from the side surface 113 of the first wavelength converter 110 and the side surface 123 of the second wavelength converter 120 can be emitted forward from the wavelength conversion unit 100 without reentering the first wavelength converter 110 and the second wavelength converter 120 by disposing the side surfaces 113 and 123 away from the reflector 160. Therefore, two wavelength-converted light beams can efficiently be emitted from the wavelength conversion unit 100, and bright illumination light can be emitted.

As described above, in the present embodiment, good color mixing is achieved, color unevenness is reduced, predetermined brightness is maintained and central intensity is increased (narrow light distribution) by setting, for example, the taper angle θt, the positions of the substantial light emission points p1 and p2 of the two wavelength converters 110 and 120 and the light distribution angle of the illumination light to have a desired relationship. For example, in the illumination apparatus 10 mounted on the specific endoscope system 1, it is necessary to emit illumination light in which the distributions of a plurality of wavelength-converted light beams are matched in a narrow range such that a distant portion is irradiated with the illumination light brightly. In the present embodiment, illumination light that satisfies this necessity can be emitted since the illumination apparatus 10 is mounted on the endoscope system 1. In order to match the light distributions of the three light components of the illumination light to narrow light distribution, it is favorable that the light distribution half-value angle of the first wavelength converted-light, the second wavelength converted-light and the first excitation light diffused light, which are emitted from the holder emission portion 154, be all 70° or less.

The wavelength conversion unit 100 with the holder 150 having a taper angle of 25° has been described so far. As for a holder having another taper angle θt, similarly, the "equal light distribution angle emission region" and "light distribution angle varying emission region" are defined in the hollow portion 152 in the holder 150.

Figure 8:
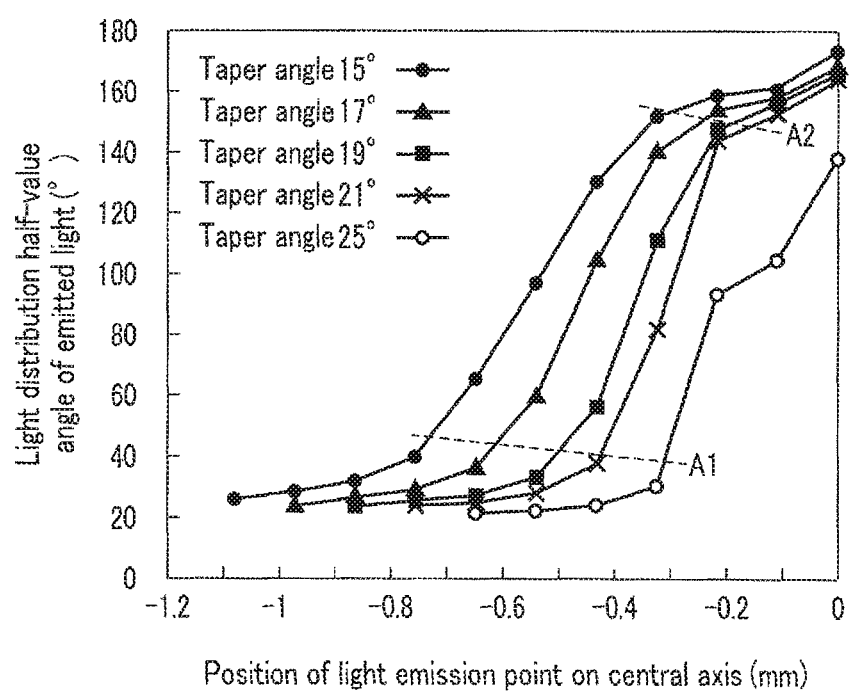
FIG. 8 is a graph showing the relationship between the light distribution half-value angle of emitted light and the position of the light emission point for each taper angle.

FIG. 8 is a graph showing the relationship between the position of the light emission point and the light distribution half-value angle of the emitted light when the taper angle θt of the holder 150 is 15°, 17°, 19°, 21° and 25°. In the graph shown in FIG. 8, the position of a light emission point having a light distribution half-value angle which is less than the value indicated by dotted line A1 is included in the "incidence portion side equal light distribution angle emission region" and the position of a light emission point having a light distribution half-value angle which is equal to or more than the value indicated by dotted line A1 and less than the value indicated by dotted line A2 is included in the "light distribution angle varying emission region." Note that the position of a light emission point having a light distribution half-value angle which is equal to or more than the value indicated by dotted line A2 is included in an "emission portion side equal light distribution angle emission region" described later.

Figure 9:
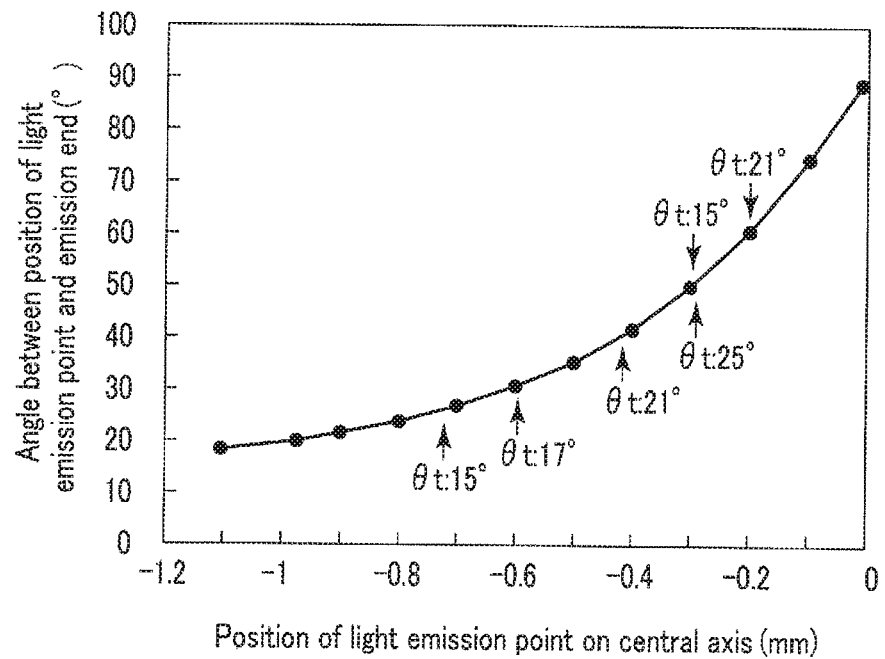
FIG. 9 is a graph showing the relationship between the angle formed by the light emission point and the emission end and the position of the light emission point at each taper angle.

FIG. 9 is a graph showing the relationship between the position of a light emission point at each taper angle θt and the angle formed by the light emission point and the emission end. As described above, a region where a line connecting the point at which the incident surface 111 of the first wavelength converter 110 and the incident surface 121 of the second wavelength converter 120 intersect the central axis C and the point on the open end of the holder emission portion 154 is equal to or less than about twice the taper angle θt, is the "incidence portion side equal light distribution angle emission region." The boundary between the "incidence portion side equal light distribution angle emission region" and the "light distribution angle varying emission region" when the taper angle θt is 15°, 17°, 21° and 25° is indicated by the arrows under the curve of the graph of FIG. 9. Note that a region where the line is about three times or more the taper angle θt is an "emission portion side equal light distribution angle emission region" described later. The boundary between the "emission portion side equal light distribution angle emission region" and the "light distribution angle varying emission region" when the taper angle θt is 15° and 21° is indicated by the arrows above the curve of the graph of FIG. 9.

[Modifications]

FIGS. 10 to 14 are diagrams schematically showing wavelength conversion units 100 according to their respective modifications 1 to 5 of the first embodiment. Modifications 1 to 5 differ from the first embodiment in the shape, arrangement, etc. of the first wavelength converter 110, the second wavelength converter 120 and the diffusion member 130 in the hollow portion 152 inside the holder 150.

Figure 10:
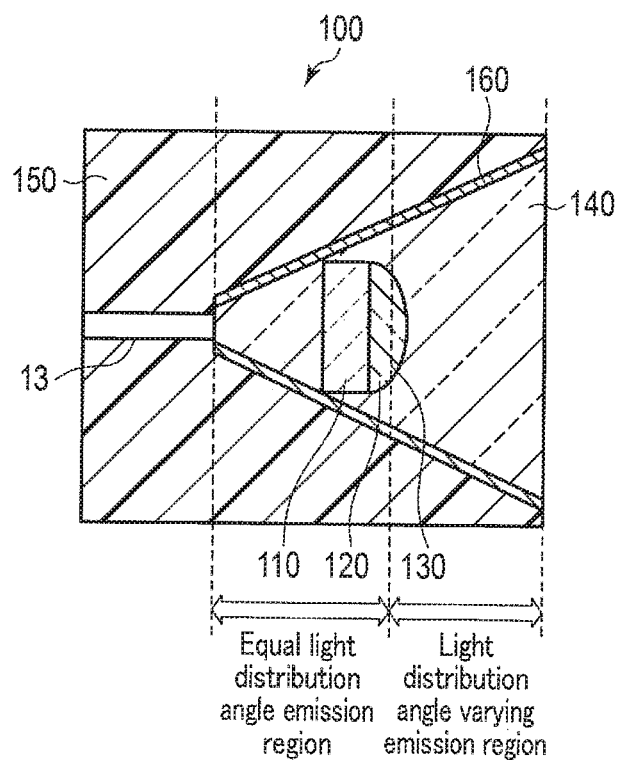
FIG. 10 is a diagram schematically showing a wavelength conversion unit according to modification 1 of the first embodiment.

In modification 1 shown in FIG. 10, the first wavelength converter 110 has the same shape as that of the first embodiment. Though the thickness of the diffusion member 130 (the second wavelength converter 120) in the central axis C is the same as that in the first embodiment, the diffusion member 130 has a convex surface. In other words, the surfaces corresponding to the emission surface 122 and side surface 123 of the second wavelength converter 120 in the first embodiment are one curved surface. If the peripheral diffusion member 130 is so reduced, it is possible to reduce a loss due to the incidence of the first wavelength-converted light on the diffusion member and the scattering thereof, and the first wavelength-converted light can be more emitted from the holder emission portion 154.

In modification 2 shown in FIG. 11, not only the substantial light emission points p1 and p2 of the first wavelength converter 110 and the second wavelength converter 120 but also the cylinder-shaped first and second wavelength converters 110 and 120 (the diffusion member 130) as a whole are disposed in the "incidence portion side equal light distribution angle emission region." Therefore, the difference in light emission angle between the two wavelength converters 110 and 120 is less than that in the first embodiment, with the result that the distributions of the two wavelength-converted light beams are easily matched.

In modification 3 shown in FIG. 12, the second wavelength converter 120 including the diffusion member 130 has a shape similar to that in the first embodiment, and the first wavelength converter 110 is shaped like a truncated cone. In this modification, the end portion of the emission surface 112 of the first wavelength converter 110 and the end portion of the incident surface 121 of the second wavelength converter 120 are in contact with the taper surface 155. Therefore, the first wavelength converter 110 is harder to incline in the holder 150 than that of the first embodiment, which is shaped like a cylinder, and thus can stably be disposed, and its central intensity angle deviation hardly occurs.

In modification 4 shown in FIG. 13, the first wavelength converter 110, the second wavelength converter 120 and the diffusion member 130 have a three-layer structure. In other words, the diffusion member 130 is separate from the second wavelength converter 120, and the first wavelength converter 110, the second wavelength converter 120 and the diffusion member 130 are stacked one on another in order from the holder incidence portion 153. In this modification, for example, a diffusion plate (a rough surface) can be used as the diffusion member 130 in addition to the diffusion particles.

In the three-layer structure described above, like the direct emission limit angle of the first wavelength-converted light and the direct emission limit angle of the second wavelength-converted light, an angle formed by the central axis C and a line connecting the center of the substantial diffusion point p3 of the diffusion member 130 and the point on the open end of the holder emission portion 154 is defined as θp3 (the direct emission limit angle of the first excitation light diffused light). Then, a difference in angle between the direct emission limit angle of the first wavelength-converted light, the direct emission limit angle of the second wavelength-converted light and the direct emission limit of the first excitation light diffused light is preferably 20° or less such that the light emission point and the diffusion point becomes close to each other.

In modification 5 shown in FIG. 14, the stacking order of the first wavelength converter 110 and the second wavelength converter 120 including the diffusion member 130 is changed. In other words, in the first embodiment, the first wavelength converter 110 is disposed beside the holder incidence portion 153, and in this modification, the second wavelength converter 120 including the diffusion member 130 is disposed beside the holder incidence portion 153. Since, therefore, the first excitation light is diffused in the diffusion member 130 and then radiated to the first wavelength converter 110, the first wavelength converter 110 becomes resistant to burning.

Note that the number of wavelength converters is not limited to two, and even if the number is three or more, the light distributions of a plurality of light components can be uniformed by setting the substantial light emission points of the wavelength converters in the "equal light distribution angle emission region".

In the first embodiment and modifications 1 to 5, the first wavelength converter 110 and the second wavelength converter 120 are in contact with each other, but they need not always be in contact with each other. For example, a transparent member such as glass may be interposed between the first wavelength converter 110 and the second wavelength converter 120. In addition, the diffusion member 130 may be mixed in the first wavelength converter 110.

Second and third embodiments will be described below. The configurations or operations of these embodiments, which are similar to those of the first embodiment, will not be described, but different points from the first embodiment will be mainly described.

[Second Embodiment]

(Configuration)

Figure 15:
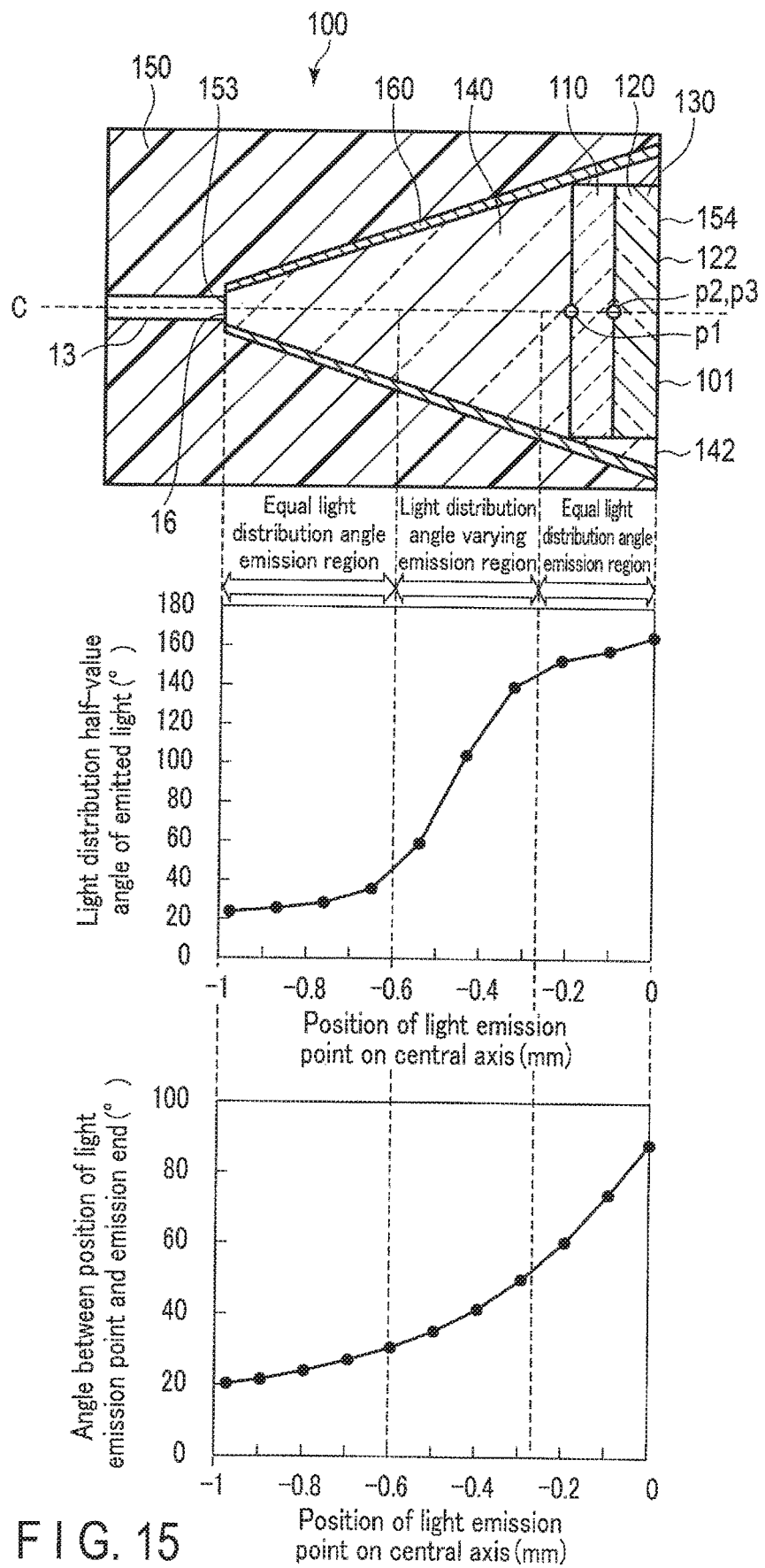
FIG. 15 is a diagram showing a wavelength conversion unit of an illumination apparatus according to a second embodiment, the relationship between the position of a light emission point of the wavelength conversion unit and the light distribution half-value angle of emitted light, and the relationship between the position of the light emission point of the wavelength conversion unit and an angle formed by the light emission point and the emission end.

FIG. 15 is a diagram showing a wavelength conversion unit 100 of an illumination apparatus 10 according to the second embodiment, the relationship between the position of a light emission point of the wavelength conversion unit 100 and the light distribution half-value angle of emitted light, and the relationship between the position of the light emission point of the wavelength conversion unit 100 and an angle formed by the light emission point and the emission end. The wavelength conversion unit 100 (holder 150) in the present embodiment has a taper angle of 17°, an incident diameter of 0.07 mm, an emission diameter of 0.7 mm and a thickness of 1.03 mm. A first wavelength converter 110 and a second wavelength converter 120 are each shaped like a cylinder and are disposed beside a holder emission portion 154. The thickness of each of the first wavelength converter 110 and the second wavelength converter 120 is 0.1 mm. The emission surface 122 of the second wavelength converter 120, the emission surface 142 of a transparent member 140 and the end face of the holder emission portion 154 are substantially flush with one another.

A diffusion member 130 is provided with diffusing particles sufficiently in high concentrations to make the light distribution angle of first excitation light substantially equal to the light distribution angle of second wavelength-converted light (for example, 18 vl %).

(Operation)

Unlike in the first embodiment, in the present embodiment, substantial light emission points p1 and p2 of the first wavelength converter 110 and the second wavelength converter 120 are located beside the holder emission portion 154 to generate first wavelength-converted light and second wavelength converted-light in the vicinity of the holder emission portion 154. Thus, the ratio of the first wavelength-converted light and the second wavelength-converted light directly emitted forward from the first wavelength converter 110 and the second wavelength converter 120 but not through a reflector 160 is increased more than in the first embodiment, and these wavelength-converted light beams are emitted as illumination light having a wide light-distribution angle.

Since the diffusion member 130 contains high-concentration diffusion particles, first excitation light radiated to the diffusion member 130 in the second wavelength converter 120 is also converted into first excitation light diffused light having a wide light distribution angle at a substantial diffusion point p3, and is emitted forward as illumination light having a wide light distribution angle like the first wavelength converted-light and the second wavelength-converted light.

In the present embodiment, as shown in FIG. 15, a region from beside a holder incidence portion 153 (the immediate vicinity of an optical fiber emission end 16) (position: −1 mm) to the vicinity of the center of a hollow portion 152 of the holder 150 (position: −0.6 mm) is defined as an "incidence portion side equal light distribution angle emission region," a region in the vicinity of the center of the hollow portion 152 (position: −0.6 mm to −0.25 mm) is defined as a "light distribution angle varying emission region" and a region from the vicinity of the center of the hollow portion 152 (position: −0.25 mm) to the end face of the holder emission portion 154 (position: 0 mm) is defined as an "emission portion side equal light distribution angle emission region." As is seen from FIG. 15, the boundary between the "incidence portion side equal light distribution angle emission region" and the "light distribution angle varying emission region" corresponds to the vicinity of about 30°, and the boundary between the "light distribution angle varying emission region" and the "emission portion side equal light distribution angle emission region" corresponds to the vicinity of about 45°.

(Advantages)

According to the present embodiment, since the substantial light emission points p1 and p2 of the two wavelength converters 110 and 120 are set beside the holder emission portion 154 whose taper angle is equal to or less than the predetermined angle, namely, in the "emission portion side equal light distribution angle emission region," two wavelength-converted light beams can be emitted from the wavelength converters 110 and 120 with their light distributions uniform as wide light distribution. Since, furthermore, the diffusion member 130 is mounted under a predetermined high-concentration condition, the first excitation light diffused light can also be emitted as illumination light of wide light distribution matched with the light distribution of the two wavelength-converted light beams. In order to make the light distributions of three light components of the illumination light uniform as wide light distribution, it is favorable that the light distribution half-value angles of the first wavelength-converted light, the second wavelength-converted light and the first excitation light diffused light emitted from the holder emission portion 154 be all 100° or more.

Since, furthermore, the distance from the optical fiber emission end 16 to the two wavelength converters 110 and 120 is longer, the diameter of a beam spot diameter of the first excitation light, formed on the incident surface 111 of the first wavelength converter 110 becomes large, thus reducing the irradiation density. This makes it possible to increase the resistance to burning of the first wavelength converter 110.

[Third Embodiment]

(Configuration)

FIG. 16 is a schematic diagram of an endoscope system 1a including an illumination apparatus 10a according to a third embodiment. In the third embodiment, the illumination apparatus 10a includes a second excitation light source 17 and an optical combiner 18 in addition to the first excitation light source 11. Like the first excitation light source 11, the second excitation light source 17 includes a laser diode (blue-violet LD) which emits blue-violet laser light (second excitation light) having an emission wavelength peak of 405 nm and a light source driving section for driving the blue-violet LD. The optical combiner 18 combines first excitation light from the first excitation light source 11 and second excitation light from the second excitation light source 17. The first excitation light source 11 and the second excitation light source 17 are connected to the base end of the optical combiner 18. An optical fiber 13 is connected to the distal end of the optical combiner 18. The first excitation light and the second excitation light combined by the optical combiner 18 are guided to a wavelength conversion unit 100 by the optical fiber 13.

The first wavelength converter 110 transmits the second excitation light without absorbing it. The second wavelength converter 120 absorbs the second excitation light and converts it into green wavelength-converted light. In other words, in the present embodiment, when the second excitation light enters the wavelength conversion unit 100, part of the second excitation light (the second excitation light diffused light) and third wavelength-converted light (green fluorescence) is emitted from the holder emission portion 154. In the present embodiment, the spectral profile of the third wavelength-converted light has characteristics that are substantially equal to those of the spectral profile of the green fluorescence (second wavelength-converted light) that is wavelength-converted by the first excitation light. The third wavelength-converted light (green fluorescence) and the second wavelength-converted light (green fluorescence), which are emitted from the holder emission portion 154, have different intensities depending upon a difference in absorption characteristics, etc. between the first excitation light and the second excitation light whose wavelengths are different. However, the present invention is not limited to this. As the first wavelength converter 110, a material (for example, a silicate-based phosphor) which also absorbs the second excitation light and then wavelength-converts it into yellow light can be used.

A light source control circuit 12 drives the first excitation light source 11 and the second excitation light source 17 independently through their respective light source driving sections. Furthermore, the light source control circuit 12 can drive the first excitation light source 11 and the second excitation light source 17 simultaneously through their respective light source driving sections to emit light therefrom.

(Operation)

In the illumination apparatus 10a of the present embodiment, an operation to be performed when only the first excitation light source 11 is driven is the same as that in the first embodiment. An operation to be performed when only the second excitation light source 17 is driven will be described below. The light source control circuit 12 drives the second excitation light source 17 based on the set light intensity information of an input section 30.

Figure 17:
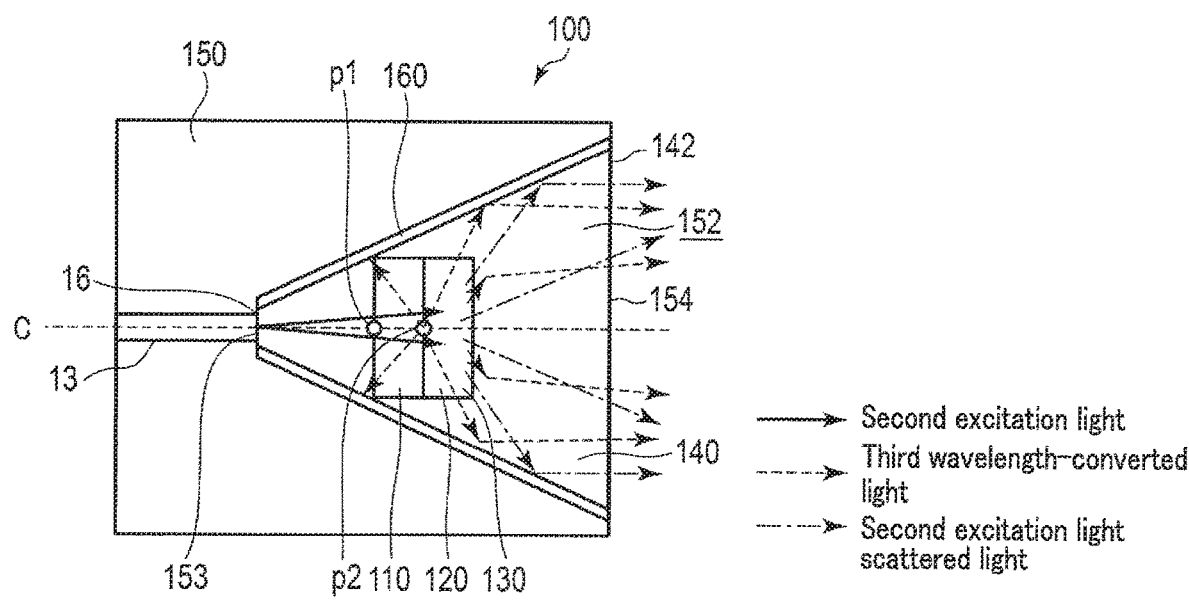
FIG. 17 is a diagram schematically showing the second excitation light, the second wavelength-converted light and the second scattered excitation light inside a holder.

An operation of generating illumination light by the wavelength conversion unit 100 will be described with reference to FIGS. 17 to 19. The second excitation light emitted from the optical fiber emission end 16 passes through the first wavelength converter 110 and is radiated to the second wavelength converter 120. The second wavelength converter 120 absorbs the radiated second excitation light and wavelength-converts it into third wavelength-converted light. Furthermore, the second excitation light radiated to a diffusion member 130 in the second wavelength converter 120 is converted into second excitation light diffused light whose light distribution angle is enlarged by a predetermined amount by the diffusion member 130.

The substantial light emission point p2 of the second wavelength converter 120 is the same as that in the first embodiment (when the first excitation light source 11 is driven). The second excitation light diffused light of the second illumination light emitted from the holder emission portion 154 of the wavelength conversion unit 100 and the third wavelength-converted light, are emitted with a narrow light distribution (light distribution half-value angle is about 65°).

Figure 18:
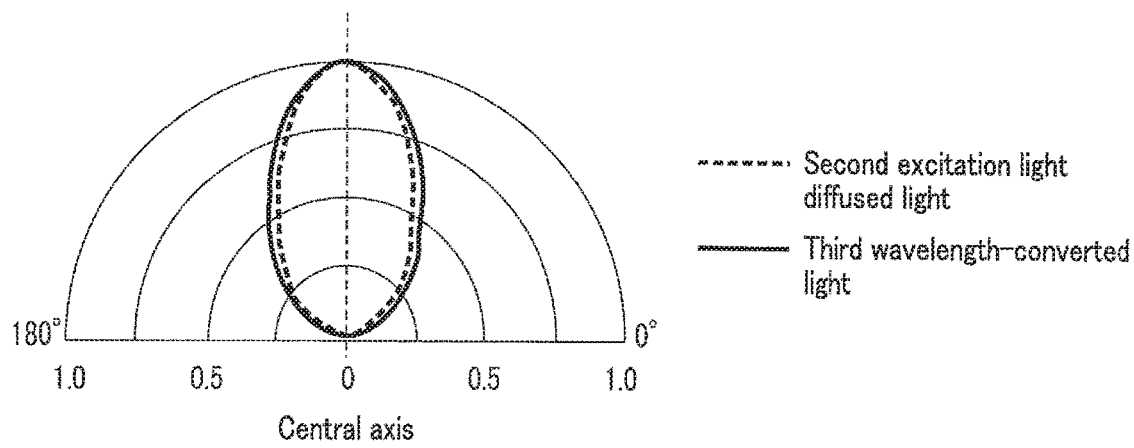
FIG. 18 is a diagram showing an example of light distribution characteristics of illumination light emitted from a wavelength conversion unit.

FIG. 18 is a diagram showing the light distribution characteristics of the second excitation light diffused light and the third wavelength-converted light, emitted from the holder emission portion 154 of the wavelength conversion unit 100. Comparing the light distribution characteristics shown in FIG. 18 with the light distribution characteristics of the illumination light (hereinafter referred to as the first illumination light) shown in FIG. 6, the second excitation light diffused light and the first excitation light diffused light exhibit substantially equal light distribution characteristics. Furthermore, the wavelength-converted light (only the third wavelength-converted light) generated by the second excitation light and the wavelength-converted light (the first wavelength-converted light and the second wavelength-converted light) generated by the first excitation light also exhibit substantially equal light distribution characteristics. Therefore, even though the first excitation light source 11 and the second excitation light source 17 are switched and controlled independently, the first illumination light and the second illumination light emitted from the illumination apparatus 10a are radiated to a subject S to be observed with substantially equal light distribution characteristics.

Figure 19:
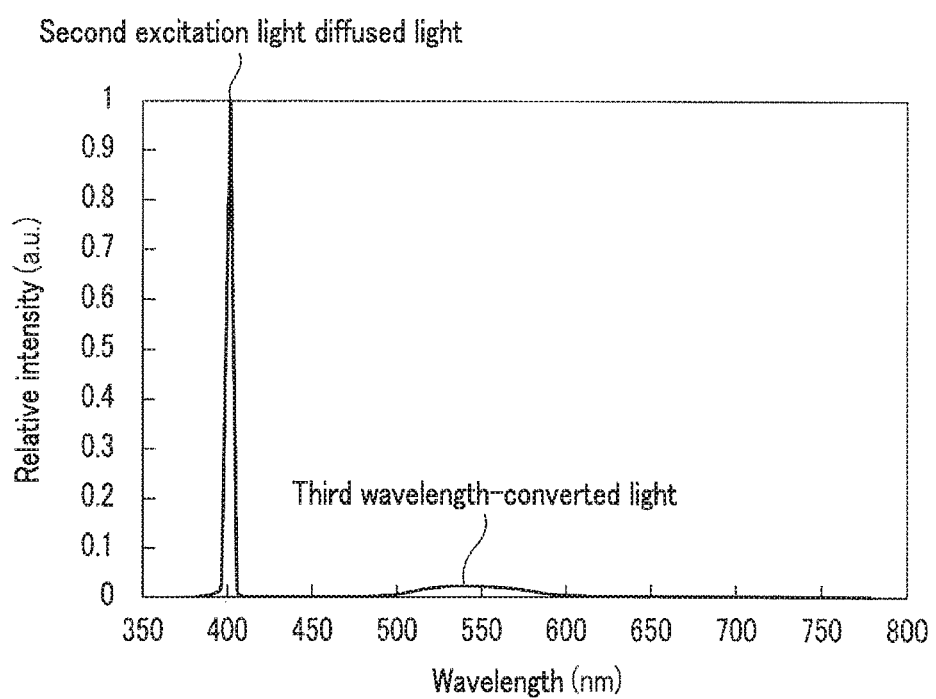
FIG. 19 is a diagram showing an example of an emission spectrum of second illumination light in the third embodiment.

FIG. 19 is a diagram showing an example of an emission spectrum of the second illumination light. The illumination light is color mixing light of the second excitation light diffused light and the third wavelength-converted light. The emission spectral profile of the second illumination light differs from that of the first illumination light, and the second illumination light exhibits light emission color characteristics that differ from those of the first illumination light.

An operation to be performed when the first excitation light source 11 and the second excitation light source 17 are driven simultaneously at a predetermined ratio will be described below. The light source control circuit 12 drives the first excitation light source 11 and the second excitation light source 17 at a predetermined ratio on the basis of the set light intensity information of the input section 30 through their respective light source driving sections.

The first excitation light and the second excitation light combined by the optical combiner 18 and guided through the optical fiber 13 enter from the holder incidence portion 153. Then, the first wavelength converter 110 converts the first excitation light into first wavelength-converted light, and the second wavelength converter 120 converts the first excitation light and the second excitation light into second wavelength-converted light and third wavelength-converted light (these two wavelength-converted light beams will be referred to as second wavelength-converted light), and the diffusion member 130 in the second wavelength converter 120 diffuses the first excitation light and the second excitation light (these will be referred to as first excitation light diffused light and second excitation light diffused light).

The substantial light emission point p1 of the first wavelength converter 110, the substantial light emission point p2 of the second wavelength converter 120 and the substantial diffusion point p3 of the diffusion member 130 are set in the incidence portion side equal light distribution angle region and thus the wavelength-converted light beams are all narrow-distributed light (FIGS. 6 and 18). Even though the light intensity ratios of the two excitation light beams are changed, the substantial light emission points p1 and p2 and diffusion points p3 remains unchanged, with the result that light distribution characteristics are maintained as uniform narrow light distribution characteristics.

(Advantages)

According to the present embodiment, the light distribution characteristics of the first illumination light generated when the first excitation light source 11 is driven and the light distribution characteristics of the second illumination light generated when the second excitation light source 17 is driven can substantially be equalized. Thus, even when a user selects the two excitation light sources 11 and 17 to switch the color of the illumination light (for example, switching between white light and special light), illumination light in which light distribution of the excitation light and that of the wavelength-converted light are substantially equal, can be achieved. Therefore, the brightness distribution of acquired images of the subject S can be prevented from varying.

Furthermore, even though the first excitation light source 11 and the second excitation light source 17 are driven at the same time to change (finely adjust) the light emission color according to the light intensity ratio of the excitation light sources 11 and 17, illumination light in which the light distribution angles of the first excitation light and the second excitation light are substantially equal and those of the first wavelength-converted light and the second wavelength-converted light are substantially equal, can be achieved. Therefore, the influence of the subject S upon the acquired images can be reduced (so that the brightness distribution does not vary).

The present invention is not limited to the foregoing embodiment described above, but it is evident to a person with ordinary skill in the art that various improvements and modifications can be made without departing from the subject matter of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illumination apparatus comprising:
a first excitation light source which emits first excitation light;
a first wavelength material which absorbs part of the first excitation light and emits first wavelength-converted light that is light in a wavelength region that differs from a wavelength region of the first excitation light;
a second wavelength material which absorbs part of the first excitation light and emits second wavelength-converted light that is light whose wavelength region differs from the wavelength region of the first excitation light and from the wavelength region of the first wavelength-converted light;
a reflector including a reflecting surface which is arranged to surround the first wavelength material and the second wavelength material, the reflector reflecting the first wavelength-converted light and the second wavelength-converted light on the reflecting surface thereof; and
a holder which holds the first wavelength material and the second wavelength material,
wherein the illumination apparatus emits a first illumination light including the first wavelength-converted light and the second wavelength-converted light reflected on the reflector, and
the holder holds the first wavelength material and at least one part of the second wavelength material in a first region among the first region and a second region, both the first and the second regions being included in a region surrounded by the reflecting surface, the first region being a region where a change in a light distribution angle of the first illumination light externally emitted from the holder is equal to or less than a predetermined value if the first wavelength material and the at least one part of the second wavelength material are arranged therein, and the second region being a region where a change in a light distribution angle of the first illumination light externally emitted from the holder is greater than the predetermined value if another part of the second wavelength material is arranged therein.

2. The illumination apparatus according to claim 1, wherein:
the first wavelength material, the second wavelength material, the holder, and the reflector comprise a wavelength conversion unit,
light distribution angles of light emitted from each of the first wavelength material and the second material are substantially equal in the first region,
the holder holds the first wavelength material and the second wavelength material such that both a substantial light emission point of the first wavelength material and a substantial light emission point of the second wavelength material are in the first region, and
the wavelength conversion unit emits the first illumination light.

3. An illumination apparatus comprising:
a first excitation light source which emits first excitation light;
a first wavelength material which absorbs part of the first excitation light and emits first wavelength-converted light that is light in a wavelength region that differs from a wavelength region of the first excitation light;
a second wavelength material which absorbs part of the first excitation light and emits second wavelength-converted light that is light whose wavelength region differs from the wavelength region of the first excitation light and from the wavelength region of the first wavelength-converted light;
a reflector including a reflecting surface which is arranged to surround the first wavelength material and the second wavelength material, the reflector reflecting the first wavelength-converted light and the second wavelength-converted light on the reflecting surface thereof; and
a holder which holds the first wavelength material and the second wavelength material,
wherein:
the illumination apparatus emits a first illumination light including the first wavelength-converted light and the second wavelength-converted light reflected on the reflector,
a first region where light distribution angles of light emitted from each of the first wavelength material and the second wavelength material have a predetermined value or less and a second region where the light distribution angle is less than the predetermined value are present in a region surrounded by the reflecting surface,
the holder holds at least one part of the first wavelength material and at least one part of the second wavelength material at the first region;
the first wavelength material, the second wavelength material, the holder, and the reflector comprise a wavelength conversion unit,
light distribution angles of light emitted from each of the first wavelength material and the second wavelength material are substantially equal in the first region,
the holder holds the first wavelength material and the second wavelength material such that both a substantial light emission point of the first wavelength material and a substantial light emission point of the second wavelength material are in the first region,
the wavelength conversion unit emits the first illumination light;
the holder comprises:
a holder incidence portion which the first excitation light enters;
a holder emission portion which emits the first wavelength-converted light and the second wavelength-converted light; and
a through hole which extends from the holder incidence portion to the holder emission portion,
the reflector is formed on an inner surface of the through hole;
the through hole and the reflecting surface are tapered such that a diameter thereof increases from the holder incidence portion to the holder emission portion;

an inclination angle formed by the inner surface on which the reflector is formed and a central axis of the through hole is defined as a taper angle; and when an inclination angle formed by the central axis and a line connecting the substantial light emission point position of the first wavelength material and a point on an open end of the holder emission portion is defined as a direct emission limit angle of the first wavelength-converted light, and an inclination angle formed by the central axis and a line connecting the substantial light emission point position of the second wavelength material and a point on the open end of the holder emission portion is defined as a direct emission limit angle of the second wavelength-converted light, the first region is an incidence portion side first region that is present closer to the holder incidence portion than the holder emission portion, the direct emission limit angle of the first wavelength-converted light and the direct emission limit angle of the second wavelength-converted light are equal to or less than twice the taper angle in the incidence portion side first region.

4. The illumination apparatus according to claim 3, wherein the wavelength conversion unit includes a diffusion member held on the central axis in the through hole, and the diffusion member converts the first excitation light into first excitation light diffused light whose light distribution angle is increased, without changing a wavelength of the first excitation light; and when an intersection of an incident surface of the diffusion member and the central axis is defined as a substantial diffusion point of the diffusion member, the substantial diffusion point of the diffusion member is set in the incidence portion side first region.

5. An illumination apparatus comprising:
   a first excitation light source which emits first excitation light;
   a first wavelength material which absorbs part of the first excitation light and emits first wavelength-converted light that is light in a wavelength region that differs from a wavelength region of the first excitation light;
   a second wavelength material which absorbs part of the first excitation light and emits second wavelength-converted light that is light whose wavelength region differs from the wavelength region of the first excitation light and from the wavelength region of the first wavelength-converted light;
   a reflector including a reflecting surface which is arranged to surround the first wavelength material and the second wavelength material, the reflector reflecting the first wavelength-converted light and the second wavelength-converted light on the reflecting surface thereof; and
   a holder which holds the first wavelength material and the second wavelength material,
   wherein:
   the illumination apparatus emits a first illumination light including the first wavelength-converted light and the second wavelength-converted light reflected on the reflector,
   a first region where light distribution angles of light emitted from each of the first wavelength material and the second wavelength material have a predetermined value or less and a second region where the light distribution angle is less than the predetermined value are present in a region surrounded by the reflecting surface,
   the holder holds at least one part of the first wavelength material and at least one part of the second wavelength material at the first region;
   the first wavelength material, the second wavelength material, the holder, and the reflector comprise a wavelength conversion unit,
   light distribution angles of light emitted from each of the first wavelength material and the second wavelength material are substantially equal in the first region,
   the holder holds the first wavelength material and the second wavelength material such that both a substantial light emission point of the first wavelength material and a substantial light emission point of the second wavelength material are in the first region,
   the wavelength conversion unit emits the first illumination light;
   the holder comprises:
      a holder incidence portion which the first excitation light enters;
      a holder emission portion which emits the first wavelength-converted light and the second wavelength-converted light; and
      a through hole which extends from the holder incidence portion to the holder emission portion,
   the reflector is formed on an inner surface of the through hole;
   the through hole and the reflecting surface are tapered such that a diameter thereof increases from the holder incidence portion to the holder emission portion; an inclination angle formed by the inner surface on which the reflector is formed and a central axis of the through hole is defined as a taper angle; and
   when an inclination angle formed by the central axis and a line connecting the substantial light emission point position of the first wavelength material and a point on an open end of the holder emission portion is defined as a direct emission limit angle of the first wavelength-converted light, and an inclination angle formed by the central axis and a line connecting the substantial light emission point position of the second wavelength material and a point on the open end of the holder emission portion is defined as a direct emission limit angle of the second wavelength-converted light,
   the first region is an emission portion side first region that is present closer to the holder emission portion than the holder incidence portion, the direct emission limit angle of the first wavelength-converted light and the direct emission limit angle of the second wavelength-converted light are equal to or more than three times the taper angle in the emission portion side first region.

6. The illumination apparatus according to claim 5, wherein the wavelength conversion unit includes a diffusion member held on the central axis in the through hole, and the diffusion member converts the first excitation light into first excitation light diffused light whose light distribution angle is increased, without changing a wavelength of the first excitation light; and when an intersection of an incident surface of the diffusion member and the central axis is defined as a substantial diffusion point of the diffusion member, the substantial diffusion point of the diffusion member is set in the emission portion side first region.

7. The illumination apparatus according to claim 4, wherein the diffusion member increases a light distribution angle of the first excitation light diffused light between a maximum angle and a minimum angle of emission angles of the first wavelength-converted light and the second wavelength-converted light emitted from the holder emission portion, a first wavelength conversion light distribution angle that is an angle at which the first wavelength-converted light is emitted from the first wavelength material, and a second wavelength conversion light distribution angle that is an angle at which the second wavelength-converted light is emitted from the second wavelength material.

8. The illumination apparatus according to claim 4, wherein the diffusion member increases a light distribution angle of the first excitation light diffused light emitted from the holder emission portion between a first wavelength conversion light distribution angle that is an angle at which the first wavelength-converted light is emitted from the first wavelength material, and a second wavelength conversion light distribution angle that is an angle at which the second wavelength-converted light is emitted from the second wavelength material.

9. The illumination apparatus according to claim 4, wherein the diffusion member is mixed with one of the first wavelength material and the second wavelength material.

10. The illumination apparatus according to claim 4, wherein a transparent region that is one of a transparent member and a gap through which the first excitation light, the first wavelength-converted light and the second wavelength-converted light pass, is disposed between an outer surface of the diffusion member and the reflector in the through hole.

11. The illumination apparatus according to claim 4, wherein the first wavelength material has a first emission surface opposed to a first incident surface of the first wavelength material that is irradiated with the first excitation light and a first side surface between the first incident surface and the first emission surface;
the second wavelength material has a second emission surface opposed to a second incident surface of the second wavelength material that is irradiated with the first excitation light and a second side surface between the second incident surface and the second emission surface; and a transparent region that is one of a transparent member and a gap through which the first excitation light, the first wavelength-converted light and the second wavelength-converted light pass, is disposed between the first and second side surfaces and the reflector in the through hole.

12. The illumination apparatus according to claim 4, wherein the first wavelength material is disposed alongside the holder incidence portion in the through hole, and the second wavelength material is disposed alongside the holder emission portion in the through hole.

13. The illumination apparatus according to claim 7, wherein the first wavelength material, the second wavelength material and the diffusion member are disposed symmetrically with regard to a diameter direction on the central axis.

14. The illumination apparatus according to claim 7, wherein the diffusion member is formed by dispersing diffusion particles in a transparent member that transmits the first excitation light, and the diffusion particles are reflective diffusion particles or transmissive diffusion particles having a refractive index that is higher than a refractive index of the transparent member; and the diffusion particles are mixed in the transparent member in a predetermined concentration such that an emission angle of the first excitation light diffused light emitted from the holder emission portion is substantially equal to an emission angle of the first wavelength material and the second wavelength-converted light.

15. The illumination apparatus according to claim 4, wherein the first wavelength converted-light, the second wavelength converted-light and the first excitation light diffused light, emitted from the holder emission portion, each have a light distribution half-value angle of 70° or less.

16. The illumination apparatus according to claim 4, wherein the first wavelength material, the second wavelength material and the diffusion member are disposed in the incidence portion side first region.

17. The illumination apparatus according to claim 6, wherein the first wavelength converted-light, the second wavelength converted-light and the first excitation light diffused light, emitted from the holder emission portion, each have a light distribution half-value angle of 100° or more.

18. The illumination apparatus according to claim 6, wherein the first wavelength material, the second wavelength material and the diffusion member are disposed in the emission portion side first region.

19. The illumination apparatus according to claim 15, wherein a difference in angle between a direct emission limit angle of the first wavelength-converted light, a direct emission limit angle of the second wavelength-converted light and a direct emission limit of the first excitation light diffused light is 20° or less.

20. The illumination apparatus according to claim 3, further comprising:
a second excitation light source which emits second excitation light;
a light source controller configured to allow the first excitation light source and the second excitation light source to be controlled independently; and
an optical combiner including an incidence end optically connected to each of the first excitation light source and the second excitation light source and an emission end optically connected to the holder incidence portion,
wherein the wavelength conversion unit receives the second excitation light, converts the second excitation light into second illumination light which differs in spectral profile from the first illumination light and emits the second illumination light, and the light source controller controls the first excitation light source and the second excitation light source to emit the first excitation light and the second excitation light to the wavelength conversion unit independently, thereby switching between the first illumination light and the second illumination light.

21. The illumination apparatus according to claim 20, wherein at least one of the first wavelength material and the second wavelength material absorbs part of the second excitation light and wavelength-converts the second excitation light; and when light generated by wavelength-converting the second excitation light is defined as third wavelength-converted light, a light distribution angle of the third wavelength-converted light is substantially equal to a light distribution angle of the first wavelength-converted light and a light distribution angle of the second wavelength-converted light.

22. The illumination apparatus according to claim 21, wherein a spectral profile of the third wavelength-converted light is substantially equal to a spectral profile of one of the first wavelength-converted light and the second wavelength-converted light.

23. The illumination apparatus according to claim 20, wherein the light source controller controls the first excitation light source and the second excitation light source to emit the first excitation light and the second excitation light simultaneously at a predetermined ratio and thus emit both the first excitation light and the second excitation light.

24. The illumination apparatus according to claim 21, wherein the wavelength conversion unit includes a diffusion member held on the central axis in the holder, and the diffusion member converts the first excitation light and the second excitation light into first excitation light diffused light and second excitation light diffused light whose light distribution angles are increased, without changing a wavelength of each of the first excitation light and the second excitation light; and when an intersection of an incident surface of the diffusion member and the central axis is defined as a substantial diffusion point of the diffusion member, the substantial diffusion point of the diffusion member is set in the first region and thus the first wavelength-converted light and the second wavelength-converted light whose light distribution angles are substantially equal are emitted.

25. The illumination apparatus according to claim 24, wherein a distribution angle of each of the first excitation light diffused light and the second excitation light diffused light emitted from the wavelength conversion unit and a distribution angle of at least one of the second wavelength-converted light and the third wavelength-converted light are substantially equal.

26. The illumination apparatus according to claim 3, wherein an intersection of a first incident surface of the first wavelength material that is irradiated with the first excitation light and the central axis is defined as a substantial light emission point position of the first wavelength material, and an intersection of a second incident surface of the second wavelength material that is irradiated with the first excitation light and the central axis is defined as a substantial light emission point position of the second wavelength material.

* * * * *